United States Patent
Lee et al.

(10) Patent No.: US 9,848,136 B2
(45) Date of Patent: Dec. 19, 2017

(54) METHOD AND APPARATUS FOR GENERATING THERMAL IMAGE

(71) Applicant: Samsung Electronics Co., Ltd., Suwon-si, Gyeonggi-do (KR)

(72) Inventors: Seung-ho Lee, Seoul (KR); Sang-hyuk Cha, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/953,166

(22) Filed: Nov. 27, 2015

(65) Prior Publication Data

US 2016/0156856 A1 Jun. 2, 2016

(30) Foreign Application Priority Data

Dec. 2, 2014 (KR) .................. 10-2014-0170829

(51) Int. Cl.
| | | |
|---|---|---|
| G01J 5/00 | (2006.01) | |
| H04N 5/33 | (2006.01) | |
| G06K 9/00 | (2006.01) | |
| A61B 5/01 | (2006.01) | |
| H04N 5/232 | (2006.01) | |
| G06T 7/246 | (2017.01) | |
| G06K 9/20 | (2006.01) | |

(52) U.S. Cl.
CPC .......... *H04N 5/332* (2013.01); *A61B 5/015* (2013.01); *G01J 5/00* (2013.01); *G06K 9/00362* (2013.01); *G06K 9/2018* (2013.01); *G06T 7/246* (2017.01); *H04N 5/23238* (2013.01); *H04N 5/23293* (2013.01); *G06T 2207/10048* (2013.01)

(58) Field of Classification Search
None
See application file for complete search history.

(56) References Cited

U.S. PATENT DOCUMENTS

| | | | | |
|---|---|---|---|---|
| 7,968,845 B1 * | 6/2011 | Wagner | ................. | G01N 25/72 250/332 |
| 2004/0154550 A1 * | 8/2004 | McQuilkin | .......... | A61B 5/0059 119/174 |
| 2007/0191729 A1 | 8/2007 | Park et al. | | |

FOREIGN PATENT DOCUMENTS

| | | |
|---|---|---|
| KR | 10-0682457 B1 | 2/2007 |
| KR | 10-2007-0057321 A | 6/2007 |

* cited by examiner

*Primary Examiner* — Edwin Gunberg
(74) *Attorney, Agent, or Firm* — Jefferson IP Law, LLP

(57) ABSTRACT

A thermal image generating apparatus for generating a thermal image regarding a target object is provided. The apparatus includes a memory configured to store a first thermal image, a first sensor, configured to measure a temperature of the target object, a second sensor configured to measure a distance to the target object, a third sensor configured to detect a movement of the thermal image generating apparatus, and a controller configured to generate a second thermal image based on temperature information received from the first sensor, distance information received from the second sensor, and movement information received from the third sensor, and generate a third thermal image based on the first thermal image and the second thermal image.

18 Claims, 21 Drawing Sheets

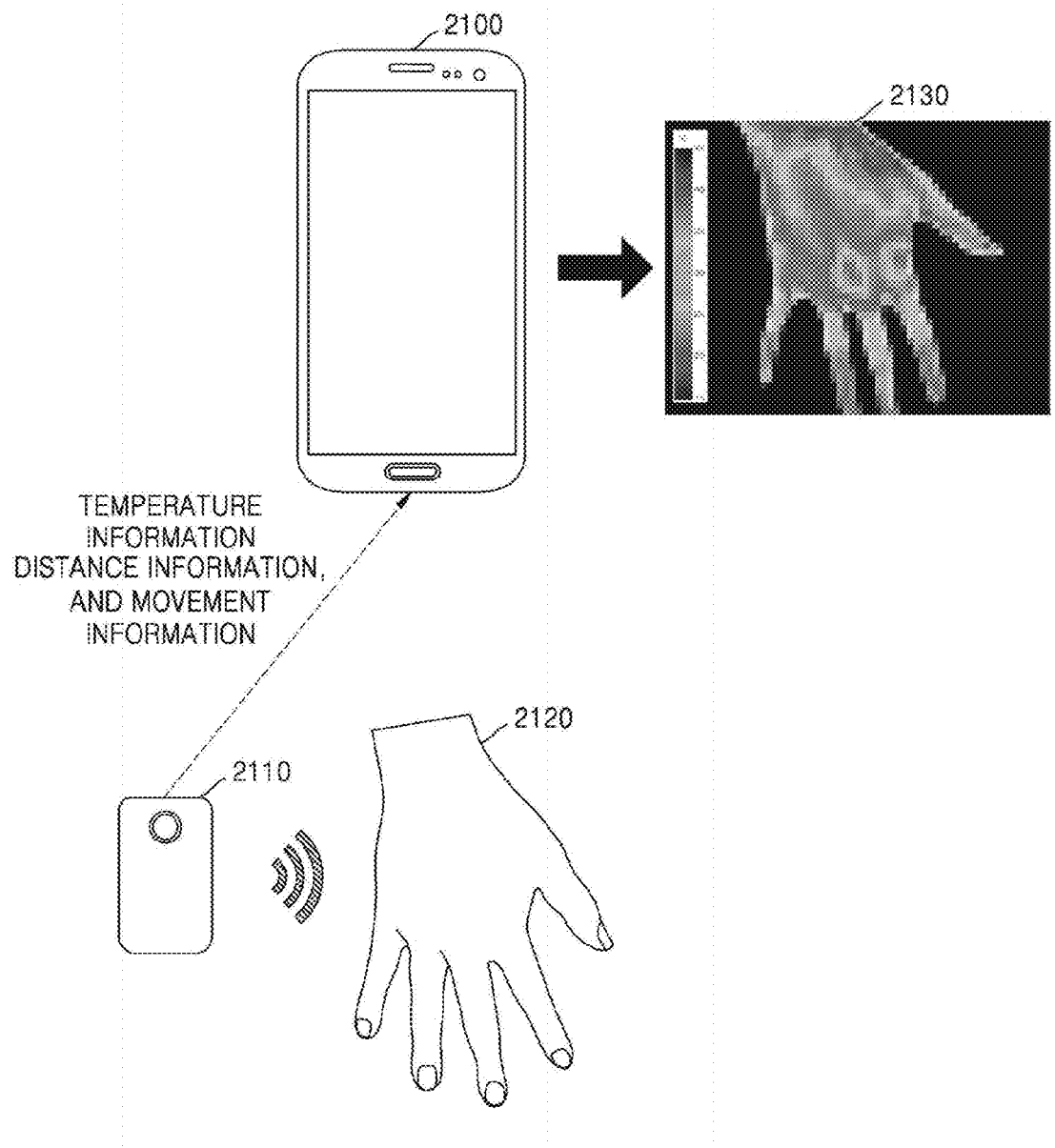

METHOD AND APPARATUS FOR GENERATING THERMAL IMAGE

CROSS-REFERENCE TO RELATED APPLICATION(S)

This application claims the benefit under 35 U.S.C. §119(a) of a Korean patent application filed on Dec. 2, 2014 in the Korean Intellectual Property Office and assigned Serial number 10-2014-0170829, the entire disclosure of which is hereby incorporated by reference.

TECHNICAL FIELD

The present disclosure relates to methods and apparatuses for generating thermal image information based on infrared rays radiated by a target object and generating a thermal image by using the thermal image information.

BACKGROUND

A thermal image indicating a temperature distribution of a target object may be generated by measuring infrared rays radiated from the target object by using an infrared ray sensor. In the case of using an infrared ray sensor, a thermal image may be generated, such that information regarding a temperature distribution of a target object that cannot be recognized by a naked eye may be obtained.

However, most thermal image generating apparatuses including such infrared ray sensors are too large to be commonly carried by a user. Furthermore, as resolution or quality of an infrared ray sensor increases, the infrared ray sensor becomes increasingly expensive. Therefore, it is difficult for an electronic device of a common user to include infrared ray sensors that are used by experts in industrial fields.

Therefore, it is necessary to provide a method and an apparatus with which common users may obtain high resolution thermal images by using temperature information regarding target objects with relatively inexpensive infrared ray sensors for mobile devices.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a thermal image generating apparatus and a thermal image generating method for generating a plurality of pieces of thermal image information based on information regarding a temperature of a target object, a distance to the target object, and a movement of a sensor, and generating a thermal image.

In accordance with an aspect of the present disclosure, a thermal image generating apparatus for generating a thermal image regarding a target object is provided. The apparatus includes a memory configured to store a first thermal image, a first sensor configured to measure temperature of the target object, a second sensor configured to measure a distance to the target object, a third sensor configured to detect a movement of the thermal image generating apparatus, and a controller configured to generate a second thermal image based on temperature information received from the first sensor, distance information received from the second sensor, and movement information received from the third sensor, and generates a third thermal image based on the first thermal image and the second thermal image.

In accordance with another aspect of the present disclosure, a thermal image generating apparatus for generating a thermal image regarding a target object is provided. The includes a memory configured to store a first thermal image, a communicator configured to receive temperature information regarding temperature of the target object, distance information regarding a distance to the target object, and movement information regarding a movement of an external sensor from the external sensor, and a controller configured to generate a second thermal image based on the temperature information, the distance information, and the movement information received from the external sensor, and generate a third thermal image based on the first thermal image and the second thermal image.

In accordance with another aspect of the present disclosure, a method of generating a thermal image regarding a target object by using a thermal image generating apparatus is provided. The method includes storing a first thermal image, processing temperature information regarding temperature of the target object, processing distance information regarding a distance between the thermal image generating apparatus and the target object, processing movement information regarding a movement of the thermal image generating apparatus, generating a second thermal image based on the processed temperature information, the processed distance information, and the processed movement information, and generating a third thermal image based on the first thermal image and the second thermal image.

In accordance with another aspect of the present disclosure, a non-transitory computer readable recording medium is provided. The non-transitory computer readable recording medium has recorded thereon a computer program for implementing the method of generating a thermal image.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 21 is a diagram illustrating a process in which a thermal image generating apparatus receives temperature information, distance information, and movement information from an external sensor and generates a thermal image according to an embodiment of the present disclosure.

Throughout the drawings, like reference numerals will be understood to refer to like parts, components, and structures.

DETAILED DESCRIPTION

Figure 1:
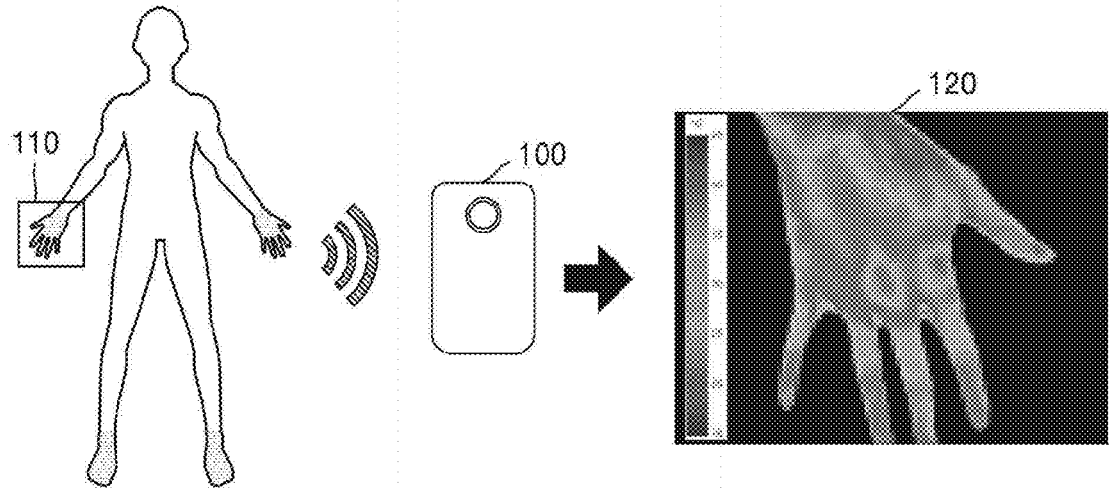
FIG. 1 is a diagram illustrating a process whereby a thermal image generating apparatus generates a thermal image by using infrared rays radiated by a target object according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein may be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In addition, unless explicitly described to the contrary, the word "comprise" and variations such as "comprises" or "comprising" will be understood to imply the inclusion of stated elements but not the exclusion of any other elements. In addition, the term "units" described in the specification mean units for processing at least one function and operation and may be implemented by software components or hardware components, such as field-programmable gate array (FPGA) or application-specific integrated circuit (ASIC). However, the "units" are not limited to software components or hardware components. The "units" may be embodied on a recording medium and may be configured to operate one or more processors.

Therefore, for example, the "units" may include components, such as software components, object-oriented software components, class components, and task components, processes, functions, properties, procedures, subroutines, program code segments, drivers, firmware, micro codes, circuits, data, databases, data structures, tables, arrays, and variables. Components and functions provided in the "units"

may be combined to smaller numbers of components and "units" or may be further divided into larger numbers of components and "units."

Reference will now be made in detail to various embodiments of the present disclosure, examples of which are illustrated in the accompanying drawings, wherein like reference numerals refer to like elements throughout. In this regard, the various embodiments of the present disclosure may have different forms and should not be construed as being limited to the descriptions set forth herein. Accordingly, the various embodiments of the present disclosure are merely described below, by referring to the figures, to explain aspects. Expressions such as "at least one of," when preceding a list of elements, modify the entire list of elements and do not modify the individual elements of the list.

FIG. 1 is a diagram illustrating a process where a thermal image generating apparatus generates a thermal image by using infrared rays radiated by a target object according to an embodiment of the present disclosure.

Referring to FIG. 1, a thermal image generating apparatus 100 may detect infrared rays radiated by a target object 110 and generate information regarding a temperature of a target object. If the target object 110 has a certain temperature, an infrared ray having a wavelength corresponding to the certain temperature is radiated. Since an infrared ray radiated from the target object is a wavelength that is not visible to a naked eye, information regarding a temperature of the target object 110 cannot be recognized by the naked eye. However, an infrared ray wavelength may be detected by using an infrared ray sensor, and a thermal image 120 may be generated by using the detected infrared ray. In the thermal image 120, temperatures may be recognized based on colors and brightness. However, although FIG. 1 illustrates that the target object 110 is a hand of a person, the target object 110 is not limited thereto, and the target object 110 may be any of various objects radiating infrared rays. For convenience of explanation, descriptions will be given based on an assumption that the target object 110 is a hand of a person.

According to an embodiment of the present disclosure, temperature information, which cannot be obtained by the naked eye of a user, may be visualized and generated as a thermal image, and such a thermal image that may be viewed via a display apparatus may be very helpful in everyday life. For example, a temperature of a hot object may be determined before touching the object with a hand, thereby preventing a burn. Furthermore, a body temperature of a living entity may act as an index indicating a health condition of the living entity. Therefore, it is necessary to measure a body temperature before diagnosis of an illness at a hospital. Currently, various techniques for remote diagnosis have been introduced, where measurement of a body temperature is inevitable for such remote diagnosis. However, it is difficult for an individual person to have an expensive thermal image generating apparatus for measuring a body temperature at a location other than a hospital. Furthermore, a highly-efficient thermal image generating apparatus is not of a portable size, and thus is inconvenient to use such a thermal image generating apparatus while on the move. The various embodiments of the present disclosure described below are embodiments for resolving the above problems and relate to a method and an apparatus for obtaining a high resolution thermal image by using a temperature sensor with a relatively low efficiency.

Figure 2:
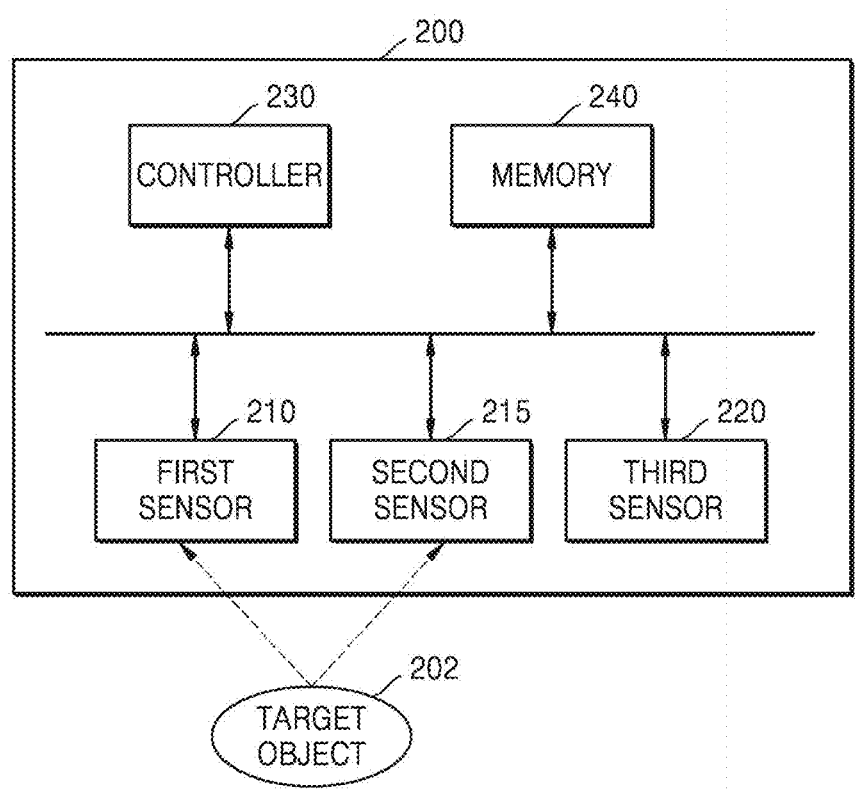
FIG. 2 is a block diagram of a thermal image generating apparatus according to an embodiment of the present disclosure.

FIG. 2 is a block diagram of a thermal image generating apparatus according to an embodiment of the present disclosure.

Referring to FIG. 2, a thermal image generating apparatus 200 includes a first sensor 210 that may measure a temperature by detecting an infrared ray radiated from a target object 202 and generate temperature information regarding the target object 202.

A second sensor 215 may measure a distance from a second sensor to the target object 202 and generate distance information.

According to an embodiment of the present disclosure, the first sensor 210 and the second sensor 215 may be included in an infrared ray sensor.

A third sensor 220 may detect a movement of the thermal image generating apparatus 200. The third sensor 220 may detect a direction and a speed of the movement of the thermal image generating apparatus 200 by measuring an acceleration of the moving thermal image generating apparatus 200. The third sensor 220 may generate movement information regarding the detected movement of the thermal image generating apparatus 200.

A controller 230 of the thermal image generating apparatus 200 may generate a plurality of pieces of thermal image information based on temperature information regarding a temperature of the target object 202 measured by the first sensor 210, distance information regarding a distance to the target object 202, and movement information regarding movement of the third sensor 220 included in the thermal image generating apparatus 200. In other words, the controller 230 may generate a plurality of pieces of thermal image information respectively based on temperature information, distance information, and movement information and may generate the thermal image 120 regarding the target object 202 based on the plurality of pieces of thermal image information and store the plurality of pieces of thermal image information in the memory 240.

Figure 3:
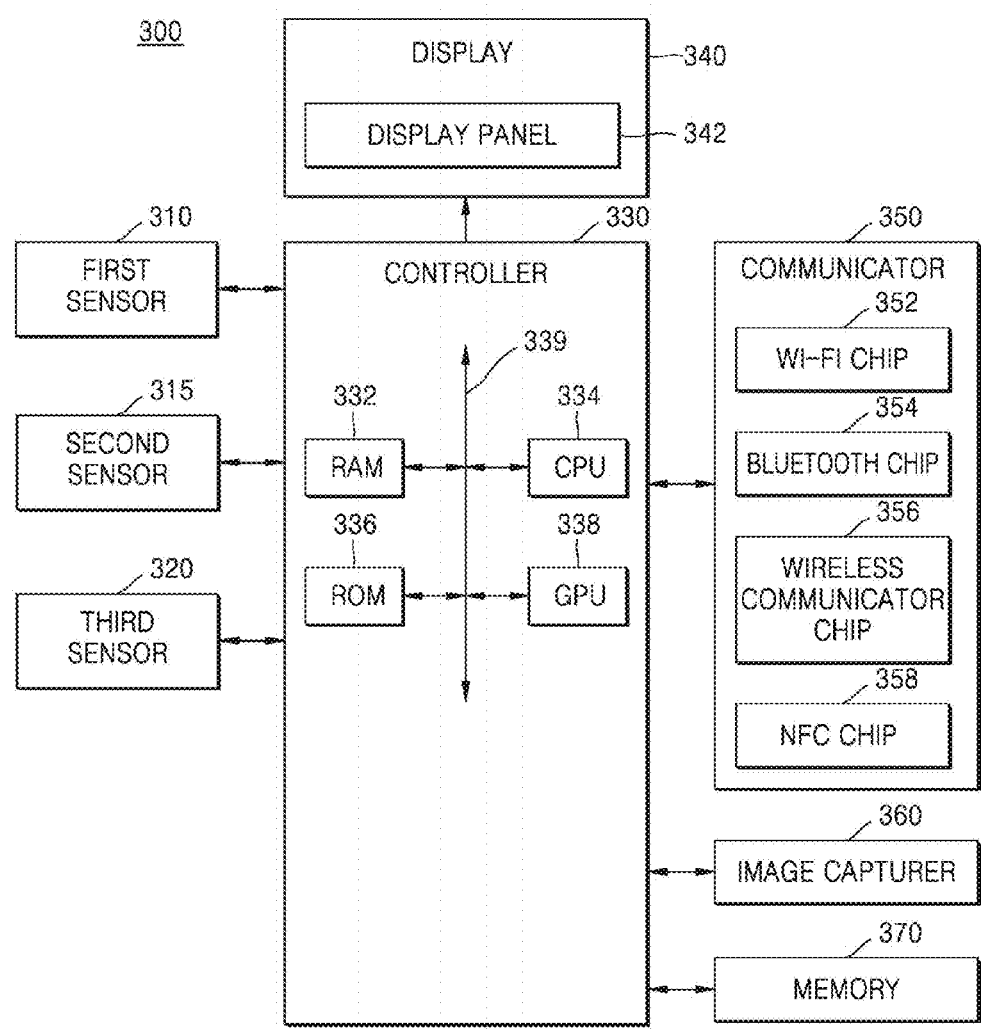
FIG. 3 is a block diagram for describing a thermal image generating apparatus according to an embodiment of the present disclosure. The thermal image generating apparatus of FIG. 3 may correspond to the thermal image generating apparatus of FIG. 2.

FIG. 3 is a block diagram for describing a thermal image generating apparatus according to an embodiment of the present disclosure. The thermal image generating apparatus of FIG. 3 may correspond to the thermal image generating apparatus 200 of FIG. 2.

Referring to FIG. 3, a thermal image generating apparatus 300 may include at least one of a first sensor 310, a second sensor, a third sensor 320, a controller 330, a display 340, a communicator 350, an image capturer 360, and a memory 370.

The first sensor 310 may measure a temperature of a target object 202. The first sensor 310 of FIG. 3 may correspond to the first sensor 210 of FIG. 2.

The second sensor 315 may measure a distance to the target object 202. The second sensor 315 of FIG. 3 may correspond to the second sensor 215 of FIG. 2.

According to an embodiment of the present disclosure, an infrared ray sensor (not illustrated) may include the first sensor 310 and the second sensor 315, where an infrared ray may be detected and a distance to the target object 202 radiating an infrared ray may be measured by using such an infrared ray sensor.

The third sensor 320 may detect a movement of the thermal image generating apparatus 300. The third sensor 320 of FIG. 3 may correspond to the third sensor 220 of FIG. 2. The thermal image generating apparatus 300 may be rotated or tilted in various directions. Here, the third sensor 320 may detect movement characteristics, such as a rotating direction, an angle, or a tilting angle, by using at least one of various sensors, such as a geomagnetic sensor, a gyro sensor, and an acceleration sensor.

The controller 330 may include at least one of a random access memory (RAM) 332, a read-only memory (ROM) 336, a central processing unit (CPU) 334, a graphics processing unit (GPU) 338, and a bus 339. The RAM 332, the ROM 336, the CPU 334, and the GPU 338 may be connected to one another via the bus 339.

The CPU 334 accesses the memory 370 and performs a booting process by using an operating system (OS) stored in the memory 370. Next, the CPU 334 performs various operations by using various programs, contents, and data stored in the memory 370.

A set of commands for booting a system is stored in the ROM 336. For example, when a turn-on command is input to the thermal image generating apparatus 300 and power is supplied thereto, the CPU 334 may boot the thermal image generating apparatus 300 by coping an OS stored in the memory 370 to the RAM 332 according to commands stored in the ROM 336 and executing the OS. When the booting process is completed, the CPU 334 copies various programs stored in the memory 370 to the RAM 332 and performs various operations by executing the programs copied to the RAM 332. When the thermal image generating apparatus 300 is booted, the GPU 338 displays a user interface (UI) screen image at a region of the display 340. In detail, the GPU 338 may generate a screen image having displayed therein an electronic document including various objects, such as contents, icons, and menus. The GPU 338 calculates property values, such as coordinates, shapes, sizes, and colors for displaying respective objects based on a layout of a screen image. Next, the GPU 338 may generate screen images of various layouts including objects based on the calculated property values. Screen images generated by the GPU 338 may be provided to the display 340 and displayed at respective regions of the display 340.

The display 340 may include a display panel 342 and a controller (not illustrated) that controls the display panel 342. The display panel 342 may be embodied with any of various types displays, such as a liquid crystal display (LCD), an organic light emitting diode (OLED), an active matrix OLED (AM-OLED), or a plasma display panel (PDP). The display panel 342 may be embodied to be flexible, transparent, or wearable. The display 340 may be combined with a touch panel (not illustrated) and provided as a touch screen (not illustrated).

The communicator 350 may communicate with various types of external devices according to various communication protocols. The communicator 350 may include at least one of a Wi-Fi chip 352, a Bluetooth chip 354, a wireless communicator chip 356, and a near field communication (NFC) chip 358. The controller 330 may communicate with various external devices via the communicator 350.

The Wi-Fi chip 352 and the Bluetooth chip 354 may perform communications according to the Wi-Fi protocol and the Bluetooth protocol. In case of using the Wi-Fi chip 352 or the Bluetooth chip 354, various connection information, such as a service set identifier (SSID) or a session key, may be transmitted and received first to establish a communication, and then various information may be transmitted and received. The wireless communicator chip 356 refers to a chip that performs communications according to various communication protocols, such as Institute of Electrical and Electronics Engineers (IEEE), ZigBee, $3^{rd}$ generation (3G), $3^{rd}$ generation partnership project (3GPP), and long term evolution (LTE). The NFC chip 358 refers to a chip that operates according to an NFC protocol that uses 13.56 MHz band from among various radio frequency identification (RF-ID) frequency bands including 135 kHz, 13.56 MHz, 433 MHz, 860~960 MHz, and 2.45 GHz.

The image capturer 360 may capture a still image or moving pictures under the control of a user. The image capturer 360 may include a plurality of image capturers, such as a front camera and a rear camera.

If the image capturer 360 is arranged, the controller 330 may perform a control operation according to a user's voice input via a microphone 360 or a user's movement recognized via the image capturer 360. For example, the thermal image generating apparatus 300 may operate in a movement-control mode or a voice-control mode. If the thermal image generating apparatus 300 operates in the movement-control mode, the controller 330 may activate the image capturer 360, capture an image of an object, trace movement changes of the object, and perform corresponding control operations.

The memory 370 may include at least one of an internal memory (not illustrated) and an external memory (not illustrated). The memory 370 of FIG. 3 may correspond to the memory 240 of FIG. 2.

For example, the internal memory may include at least one of a volatile memory (e.g., a dynamic RAM (DRAM), a static RAM (SRAM), a synchronous DRAM (SDRAM), and the like), a non-volatile memory (e.g., a one-time programmable ROM (OTPROM), a PROM, an erasable and programmable ROM (EPROM), an electrically erasable and programmable ROM (EEPROM), a mask ROM, a flash ROM, and the like), a hard disk drive (HDD), or a solid state drive (SSD). According to an embodiment of the present disclosure, the CPU 224 may load a command or data received from at least one of a non-volatile memory and another component to a volatile memory and process the command or the data. Furthermore, the CPU 224 may store data received from or generated by another component in a non-volatile memory.

For example, the external memory may include at least one of a compact flash (CF), a secure digital (SD), a micro-SD, a mini-SD, an extreme digital (XD), and a memory stick.

The memory 370 may store various programs and data used for operations of the thermal image generating apparatus 100. For example, the memory 370 may store at least a portion of content to be displayed on a lock screen image temporarily or permanently.

Figure 4:
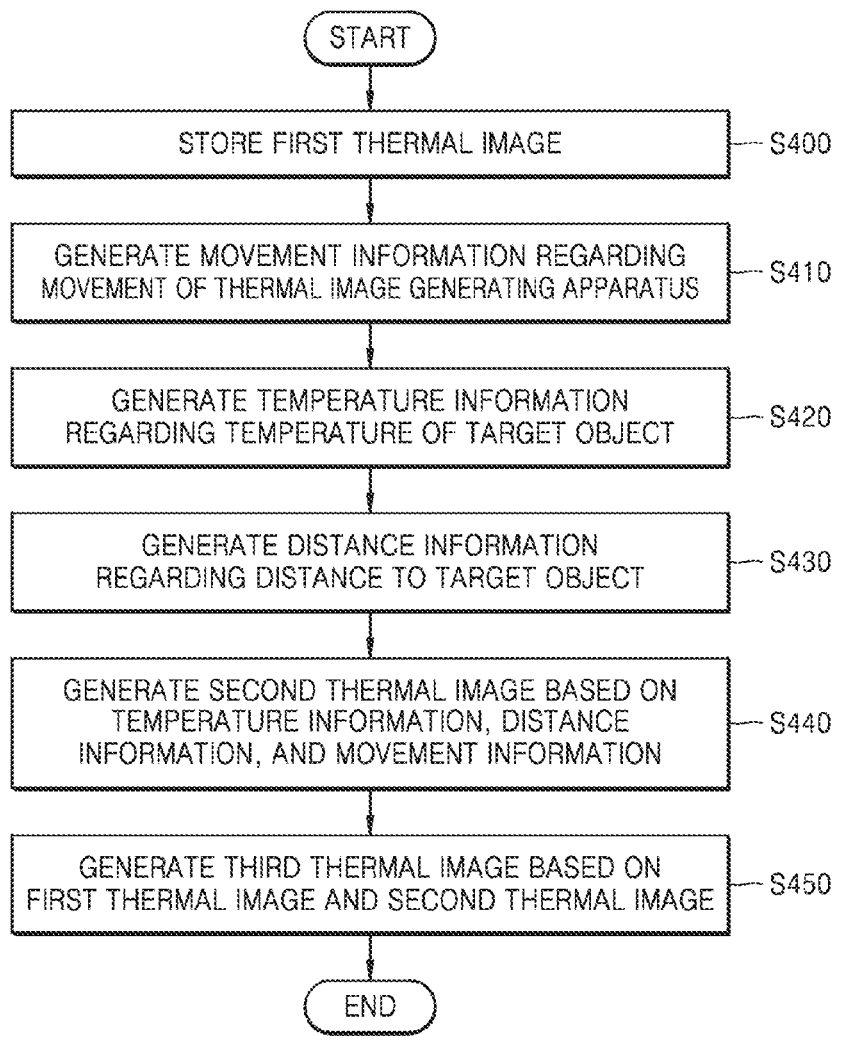
FIG. 4 is a flowchart of a method of generating a thermal image according to an embodiment of the present disclosure.

FIG. 4 is a flowchart of a method of generating a thermal image according to an embodiment of the present disclosure.

Referring to FIG. 4, in operation S400, the thermal image generating apparatus 200 may store a first thermal image in the memory 240. According to an embodiment of the present disclosure, the first thermal image may be a thermal image generated by the thermal image generating apparatus 200 by using a method of generating a thermal image according to an embodiment of the present disclosure.

In operation S410, the thermal image generating apparatus 200 may generate movement information by detecting a movement of the thermal image generating apparatus 200 by using the third sensor 220. According to an embodiment of the present disclosure, the controller 230 of the thermal image generating apparatus 200 may detect a direction and an acceleration of a movement of the thermal image generating apparatus 200 so as to calculate how much the thermal image generating apparatus 200 is moved. According to an embodiment of the present disclosure, the movement information may be used to determine a location of the second thermal image, which is determined in the third thermal image based on the first thermal image, in a process for generating the third thermal image of the controller 230 later.

In operation S420, the thermal image generating apparatus 200 may generate temperature information by measuring temperature of the target object 202 by using the first sensor 210. The temperature information may become a standard for displaying colors and brightness corresponding to temperatures of the target object 202 in thermal images to be generated later.

In operation S430, the thermal image generating apparatus 200 may generate distance information by measuring a distance between the target object 202 and the second sensor 215 of the thermal image generating apparatus 200 by using the second sensor 215. The distance information may become a standard for determining a distance from the target object 202 at which the temperature information generated in the operation S420 is measured and determining a size of a second thermal image to be displayed during generation of a third thermal image later.

In operation S440, the controller 230 of the thermal image generating apparatus 200 may generate the second thermal image based on the temperature information, the distance information, and the movement information. The second thermal image may be expressed as a thermal image regarding a portion of the target object 202 that is generated based on temperature information regarding the target object 202, distance information regarding the target object 202, and movement information regarding the thermal image generating apparatus 200 that are measured at particular time intervals.

In operation S450, the controller 230 of the thermal image generating apparatus 200 may generate a third thermal image based on the first thermal image stored in the operation S400 and the second thermal image generated in the operation S440. The first thermal image and the second thermal image constituting the third thermal image may be displayed on the display 340 as connected images. Detailed descriptions thereof will be given below.

Figure 5:
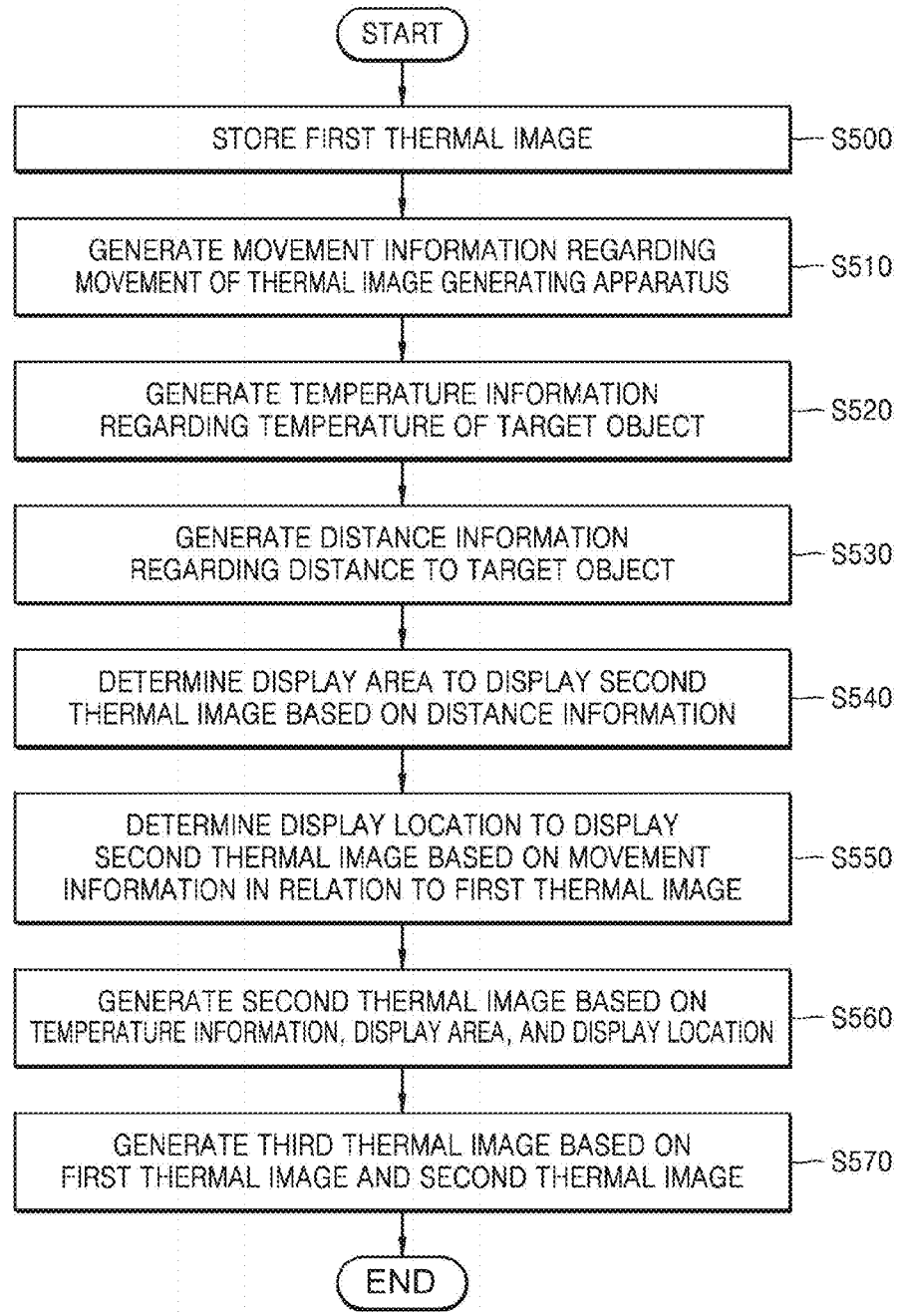
FIG. 5 is a flowchart of a method of generating a thermal image in which respective operations using temperature information, distance information, and movement information are illustrated in detail according to an embodiment of the present disclosure.

FIG. 5 is a flowchart of a method of generating a thermal image according to an embodiment of the present disclosure, in which respective operations using temperature information, distance information, and movement information are illustrated in detail.

Referring to FIG. 5, in operation S500, the thermal image generating apparatus 200 may store a first thermal image in the memory 240. According to an embodiment of the present disclosure, the first thermal image may be a thermal image generated by the thermal image generating apparatus 200 by using a method of generating a thermal image according to an embodiment of the present disclosure.

Figure 7:
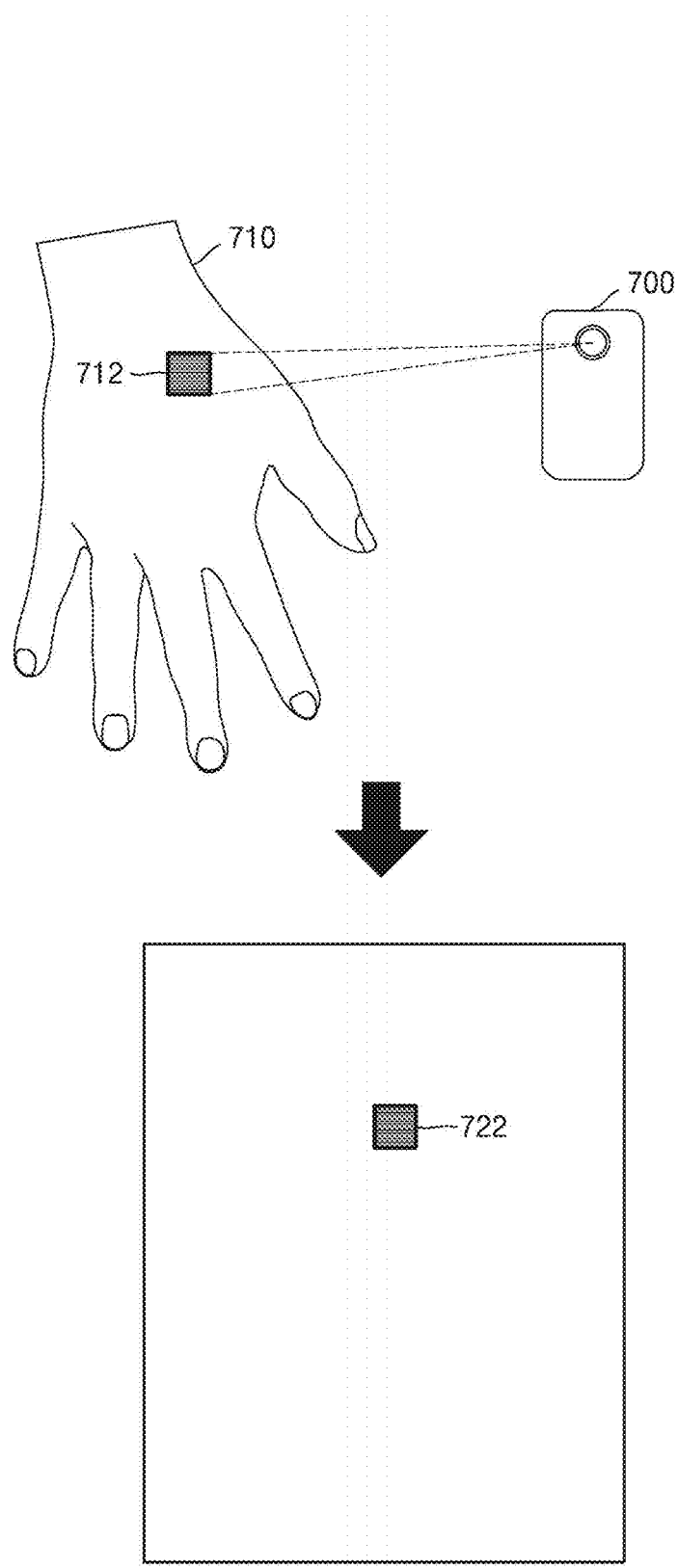
FIG. 7 is a diagram illustrating a process whereby a thermal image generating apparatus stores a first thermal image when the thermal image generating apparatus obtains temperature information and generates a third thermal image according to an embodiment of the present disclosure.

FIG. 7 illustrates a process that a thermal image generating apparatus according to an embodiment of the present disclosure stores a first thermal image when the thermal image generating apparatus obtains temperature information and generates a third thermal image.

Referring to FIG. 7, a thermal image generating apparatus 700 of FIG. 7 may correspond to the thermal image generating apparatus 200 of FIG. 2. The thermal image generating apparatus 700 may store a thermal image corresponding to a reference numeral 722 in the memory 240 as a first thermal image. In operation S510, the thermal image generating apparatus 200 may generate movement information regarding a movement of the thermal image generating apparatus 200 by using the third sensor 220. Since the operation S510 may correspond to the operation S410 of FIG. 4, detailed descriptions thereof will be omitted.

In operation S520, the thermal image generating apparatus 200 may generate temperature information regarding temperature of the target object 202 by using the first sensor 210. Since the operation S520 may correspond to the operation S420 of FIG. 4, detailed descriptions thereof will be omitted.

In operation S530, the thermal image generating apparatus 200 may generate distance information regarding a distance between the thermal image generating apparatus 200 and the target object 202 by using the second sensor 215. Since the operation S530 may correspond to the operation S430 of FIG. 4, detailed descriptions thereof will be omitted.

Operations S540 and S550 below illustrate how temperature information, distance information, and movement information are reflected to generation of a thermal image in the operation S450 of FIG. 4 in detail.

In operation S540, the thermal image generating apparatus 200 may determine a display area of a second thermal image based on the distance information generated in the operation S530.

Figure 6:
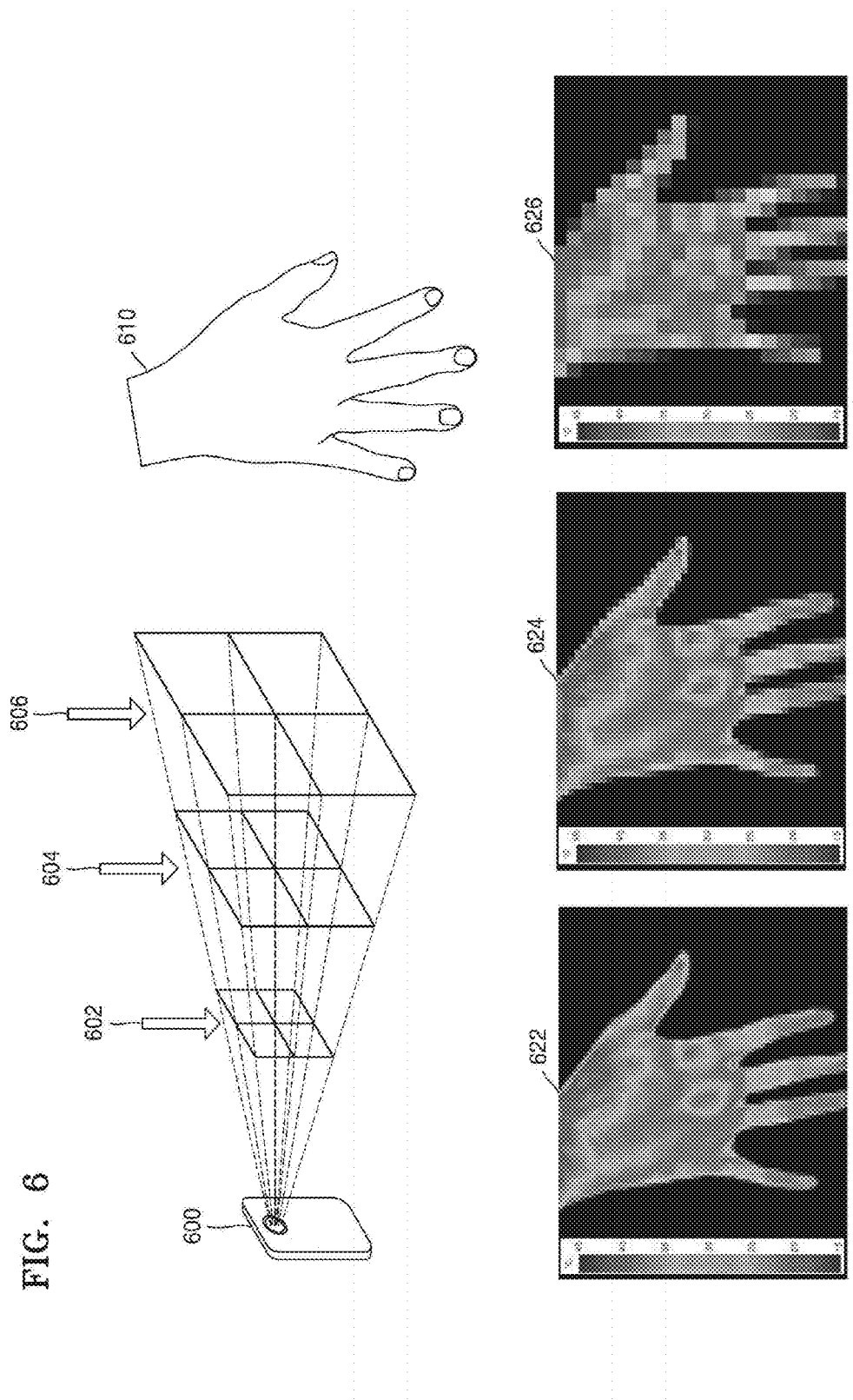
FIG. 6 is a diagram for describing how a third thermal image is displayed according to various distances between a thermal image generating apparatus according to an embodiment of the present disclosure and a target object.

FIG. 6 is a diagram for describing how a third thermal image is displayed according to various distances between a thermal image generating apparatus according to an embodiment of the present disclosure and a target object. The thermal image generating apparatus of FIG. 6 may correspond to the thermal image generating apparatus 200 of FIG. 2.

Referring to FIG. 6, when a target object 610 is located by a thermal image generating apparatus 600 at a first location 602, a second location 604, or a third location 606 and a distance from the first sensor 210 to the first location 602 is a, a distance to the second location 604 may be expressed as 2a, whereas a distance to the third location 606 may be expressed as 3a. In this case, if an area that the thermal image generating apparatus 600 may measure temperature when the target object 610 is located at the first location 602 is b, areas that the thermal image generating apparatus 600 may measure temperatures when the target object 610 is located at the second location 604 and the third location 606 may be 4b and 9b, respectively. In other words, a temperature measuring area of the thermal image generating apparatus 600 is proportional to the square of a distance to the target object 610. An area in a thermal image in which temperature information corresponding to thermal image information may be proportional to the square of a distance between the second sensor 215 of the thermal image generating apparatus 600 and a portion of the target object 610 to be measured (e.g., a first location 602). For example, if the target object 610 is located at the first location 602 and temperature of the target object 610 is measured while a distance to the first location 602 is maintained constant, the thermal image generating apparatus 600 may generate a first thermal image 622. If the target object 610 is located at the second location 604 and temperature of the target object 610 is measured while a distance to the second location 604 is maintained constant, the thermal image generating apparatus 600 may generate a second thermal image 624. In this case, the second thermal image 624 regarding the second location 604 may be less precise than the first thermal image 622 regarding the first location 602. The reason thereof is that, since an area for measuring temperature is smaller when the target object 610 is located at the first location 602 than when the target object 610 is located at the second location 604, areas for displaying respective second thermal images on the first thermal image 622 regarding the first location 602 are relatively smaller than areas for displaying respective second thermal images on the second thermal image 624 regarding the second location 604. If the target object 610 is located at the third location 606 and temperature of the target object 610 is measured while a distance to the third location 606 is maintained constant, the thermal image generating apparatus 600 may generate a third thermal image 626. In this case, the third thermal image 626 regarding the third location 606 may be less precise than the second thermal image 624 regarding the third second location 604. The reason thereof is that, since an area for measuring temperature is smaller when the target object 610 is located at the second location 604 than when the target object 610 is located at the third location 606, areas for displaying respective second thermal images on the second thermal image 624 regarding the second location 604 are relatively smaller than areas for displaying respective second thermal images on the third thermal image 626 regarding the third location 606.

In operation S550, the thermal image generating apparatus 200 may determine a location to display thermal image information on a thermal image based on the movement information generated in the operation S510. The thermal image generating apparatus 700 may measure temperature and a distance with respect to a target object 710 and detect a movement of the thermal image generating apparatus 700 by using the first sensor 210 at the same time. In detail, the controller 230 of the thermal image generating apparatus 700 may determine an arbitrary point as a reference point and measure a direction in which the thermal image generating apparatus 700 moves and an acceleration of a movement of the thermal image generating apparatus 700 at a constant interval, thereby determining location of the thermal image generating apparatus 700 after a certain period of time in relation to the reference point. In the operation S500, the thermal image generating apparatus 700 could store the first thermal image 722 in the memory 240. If the thermal image generating apparatus 700 measures temperature of a target object 710, the thermal image generating apparatus 700 may measure temperature of a portion of the target object 710 instead of measuring temperature of the entire target object 710 at once. The controller 230 of the thermal image generating apparatus 700 may generate a second thermal image based on the temperature information, the distance information, and the movement information. In this case, a location to display the second thermal image may be determined based on the movement information in relation to the first thermal image, which is a reference point.

Figure 8:
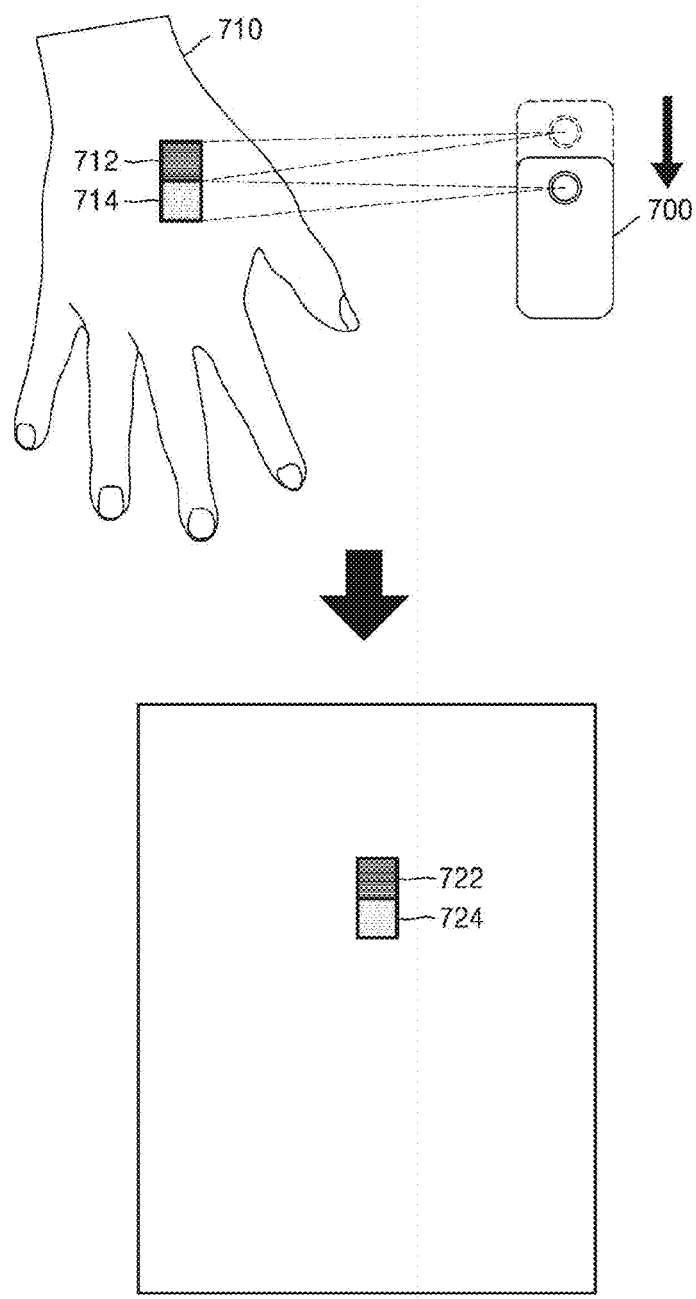
FIG. 8 is a diagram illustrating that a location to display a second thermal image in relation to a first thermal image is determined as a thermal image generating apparatus moves and obtains temperature information according to an embodiment of the present disclosure.

FIG. 8 is a diagram illustrating that a location to display a second thermal image in relation to a first thermal image is determined as a thermal image generating apparatus according to an embodiment of the present disclosure moves and obtains temperature information.

Referring to FIG. 8, in detail, the thermal image generating apparatus 700 may measure temperatures of portions (e.g., portions corresponding to reference numerals 712 and 714) of the target object 710 and generate thermal images regarding the respective portions. According to an embodiment of the present disclosure, the thermal image generating apparatus 700 may measure temperature of the portion corresponding to the reference numeral 712 and move to another point. The thermal image generating apparatus 700 may measure information regarding a movement of the thermal image generating apparatus 700, such as an acceleration and a moving direction, via the third sensor 220. By using the movement information measured via the third sensor 220, the controller 230 of the thermal image generating apparatus 700 may determine a location of the thermal image generating apparatus 700 on the target object 710 after a certain time interval.

Referring to FIG. 8, the thermal image generating apparatus 700 may move from a first location 712, which is a reference point, to another point (e.g., a point corresponding to the reference numeral 714) and measure temperature of the other point (the point corresponding to the reference numeral 714). Based on movement information based on such a movement, the thermal image generating apparatus 700 may determine a location to display a second thermal image that is generated based on temperature and a distance measured in relation to the other point (the point corresponding to the reference numeral 714) in relation to the first thermal image. In other words, if movement information generated by the third sensor 220 is information corresponding to a downward movement of the thermal image generating apparatus 700, the second thermal image may be displayed below the first thermal image.

In operation S560, the thermal image generating apparatus 700 may generate a second thermal image based on temperature information, an area to be displayed, and a location to be displayed. According to an embodiment of the present disclosure, a second thermal image 724 may be generated based on temperature information, distance information, and movement information generated by the thermal image generating apparatus 700 after the thermal image generating apparatus 700 moves to the point corresponding to the reference numeral 714 that is vertically below the reference point corresponding to the reference numeral 712. In this case, the second thermal image 724 may be displayed vertically below the first thermal image 722.

In operation S570, the thermal image generating apparatus 200 may generate a third thermal image. Since the operation S570 may correspond to the operation S450 of FIG. 4, detailed descriptions thereof will be omitted.

Referring to FIG. 6, even if an actual temperature of the target object 610 is constant, the third thermal images may be displayed differently, because a value of the temperature information, an area for displaying the temperature information, and a position for displaying the temperature information in the third thermal image vary according to a distance, and a position of measuring the temperature of the target object 610. Thermal images corresponding to the reference numerals 622, 624, and 626 generated based on thermal image information by the thermal image generating apparatus 700 with respect to the same target object 610 at different distances may exhibit different precisions.

Figure 9:
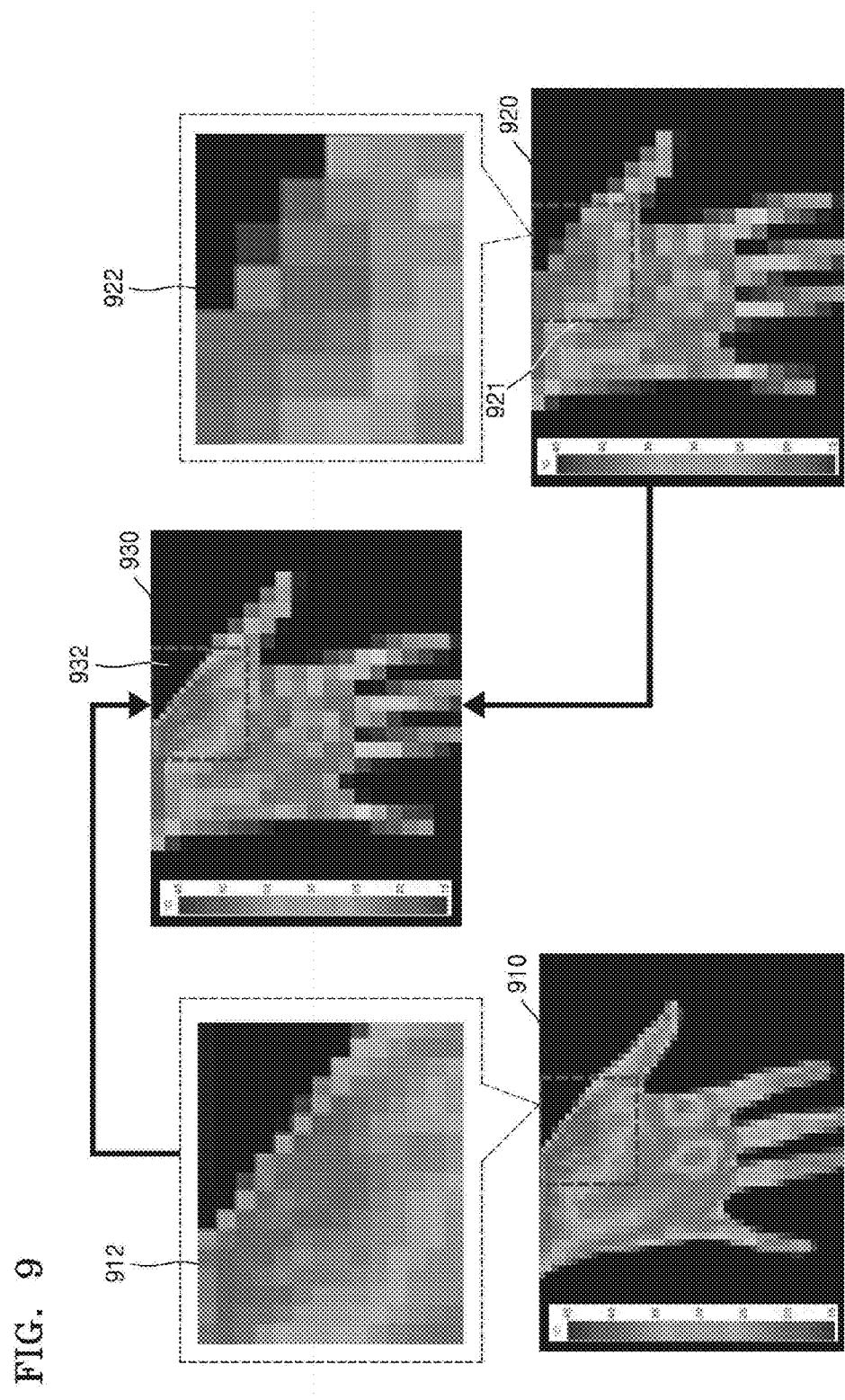
FIG. 9 is a diagram illustrating that a thermal image generating apparatus generates a thermal image when a plurality of pieces of thermal image information are generated with respect to a same location of a target object at different distances from the target object according to an embodiment of the present disclosure.

FIG. 9 is a diagram illustrating that a thermal image generating apparatus according to an embodiment of the present disclosure generates a thermal image when a plurality of pieces of thermal image information are generated with respect to a same location of a target object at different distances from the target object.

Referring to FIG. 9, as described above with reference to FIG. 6, precision of a thermal image generated by the thermal image generating apparatus 600 varies according to distance information, which is information regarding a distance between the target object 610 and the thermal image generating apparatus 600. In other words, the smaller the distance is, the higher the precision of a thermal image may be. However, if the distance is small, precision increases, but it may take a relatively long time to measure the entire target object 610 as compared to a case where the distance is large. Therefore, even if the target object 610 is measured at a relatively large distance, if a precise temperature measurement is demanded at a certain portion of the target object 610, it is necessary to generate a thermal image based on a precise temperature measurement regarding the portion.

The thermal image generating apparatus 200 according to an embodiment of the present disclosure may measure temperature at a distance a and generate a thermal image corresponding to the reference numeral 910 and may also measure temperature at a distance b, which is greater than the distance a, and generate a thermal image corresponding to the reference numeral 920. The thermal image corresponding to the reference numeral 920 that is generated by measuring temperature at the distance b greater than the distance a is less precise than the thermal image corresponding to the reference numeral 910 that is generated by measuring temperature at the distance a. Thermal images corresponding to the reference numerals 912 and 922 are magnified images of portions of same locations in thermal images corresponding to the reference numerals 910 and 920. The thermal image corresponding to the reference numeral 912 may illustrate a more detailed temperature measurement than the thermal image corresponding to the reference numeral 922. According to an embodiment of the present disclosure, the thermal image generating apparatus 200 may generate a second thermal image with respect to a particular location of the target object 202. However, if the thermal image generating apparatus 200 generated a new second thermal image overlapping an already stored first thermal image by measuring temperature at a closer distance, the new second thermal image may be used to generate the third thermal image, instead of the stored first thermal image. Furthermore, if a new thermal image is generated at the overlapped location, a third thermal image may be generated by using temperature information regarding the previously generated first thermal image and temperature information regarding the newly generated second thermal image. For example, an average value of the temperature information regarding the first thermal image and the temperature information regarding the second thermal image may become temperature information regarding the third thermal image at the overlapped location.

The thermal image generating apparatus 200 may already store a first thermal image 920. However, a second thermal image 912 may be displayed by precisely measuring temperature at a closer distance to the stored first thermal image 920. When the second thermal image 912 is compared to the overlapping portion 922 at which the first thermal image 920 overlaps the second thermal image 912, the second thermal image 912 may indicate more precise temperature measurement. In other words, even if the first thermal image 920 regarding a particular location 921 of the target object 202 is already stored, the thermal image generating apparatus 200 may measure temperature precisely at a closer distance to the particular location 921, generate the second thermal image 912 regarding the particular location 921 of the first thermal image 920, and generate a third thermal image 930 including more precise temperature information at a particular location 932.

Figure 10:
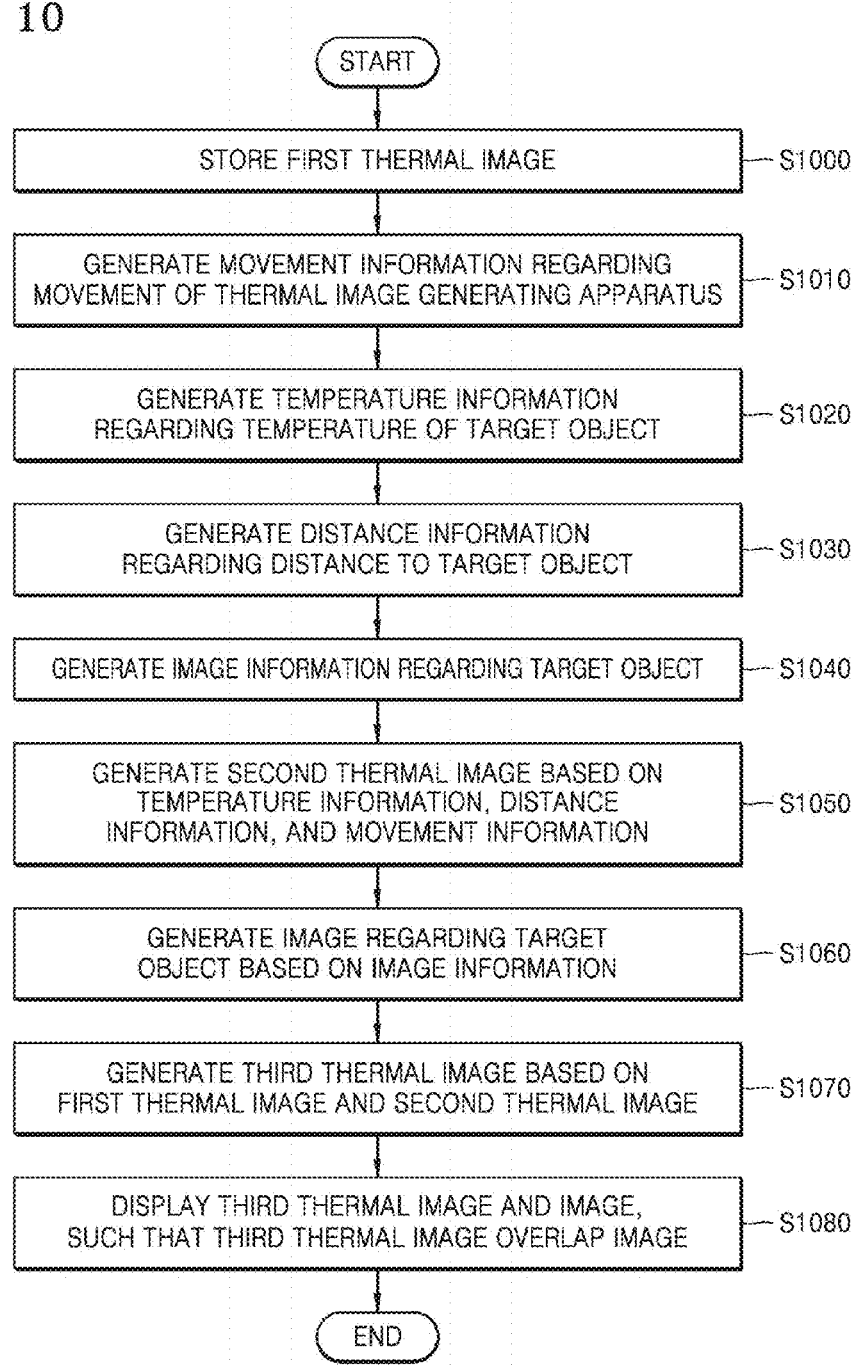
FIG. 10 is a flowchart illustrating a method of generating a thermal image, in which the thermal image regarding a temperature distribution of a target object and an image of the target object captured by an image capturer using visible rays are obtained and the thermal image and the image are displayed to overlap each other according to an embodiment of the present disclosure.

FIG. 10 is a flowchart illustrating a method of generating a thermal image, in which a thermal image regarding temperature of a target object and an image of the target object captured by an image capturer using visible rays are obtained and the thermal image and the image are displayed to overlap each other according to an embodiment of the present disclosure.

Referring to FIG. 10, in detail, the thermal image generating apparatus 200 may not only generate a thermal image regarding the target object 202, but also obtain an image based on visible rays by using the image capturer 360.

Furthermore, as the thermal image generating apparatus 200 displays a thermal image and an image to overlap each other, the thermal image may be compared to the image later.

In operation S1000, the thermal image generating apparatus 200 may store a first thermal image in the memory 240. Since the operation S1000 may correspond to the operation S400 of FIG. 4, detailed descriptions thereof will be omitted.

In operation S1010, the thermal image generating apparatus 200 may generate movement information regarding a movement of the thermal image generating apparatus 200 by using the third sensor 220. Since the operation S1010 may correspond to the operation S410 of FIG. 4, detailed descriptions thereof will be omitted.

In operation S1020, the thermal image generating apparatus 200 may generate temperature information regarding temperature of the target object 202 by using the target object 202. Since the operation S1020 may correspond to the operation S420 of FIG. 4, detailed descriptions thereof will be omitted.

In operation S1030, the thermal image generating apparatus 200 may generate distance information regarding a distance to the target object 202 by using the second sensor 215. Since the operation S1030 may correspond to the operation S430 of FIG. 4, detailed descriptions thereof will be omitted.

In operation S1040, the thermal image generating apparatus 200 may generate image information regarding the target object 202. In detail, the controller 230 of the thermal image generating apparatus 200 may capture an image of a portion of the target object 202 corresponding to the temperature information generated in the operation S1020, thereby generating image information regarding the corresponding portion. According to an embodiment of the present disclosure, the first sensor 210 and the second sensor 215 may be included in an infrared ray sensor (not illustrated). Furthermore, according to an embodiment of the present disclosure, a single element including a combination of such an infrared ray sensor and a red, green, blue (RGB) sensor may receive not only infrared rays, but also visible rays, and generate image information regarding the visible rays. In this case, each pixel may be an RGB pixel or a pixel for sensing an infrared ray. In other words, by using the infrared ray sensor (not illustrated), the first sensor 210 of the thermal image generating apparatus 200 may measure temperature of the target object 202 and generate temperature information in the operation S1010, whereas the second sensor 215 of the thermal image generating apparatus 200 may measure a distance between the target object 202 and the second sensor 215. Furthermore, such an infrared ray sensor (not illustrated) may also receive visible rays reflected by the target object 202 and generate image information regarding the target object 202.

In operation S1050, the controller 230 of the thermal image generating apparatus 200 may generate a second thermal image based on the movement information generated in the operation S1010, the temperature information generated in the operation S1020, and the distance information generated in the operation S1030. Since the operation S1050 may correspond to the operation S440 of FIG. 4, detailed descriptions thereof will be omitted.

In operation S1060, the thermal image generating apparatus 200 may generate an image of the target object 202. In detail, the controller 230 may generate an image of the target object 202, which is similar to a naked-eye view of the target object 202, by using the image information generated in the operation S1040. If an infrared ray sensor (not illustrated) including the first sensor 210 and the second sensor 215 receives both visible rays and infrared rays according to an embodiment of the present disclosure, an optical error between a thermal image and an image which is generated by capturing the visible rays is small, and thus it may be easy to compare and analyze the image and the thermal image.

In operation S1070, the controller 230 of the thermal image generating apparatus 200 may generate a third thermal image based on the first thermal image stored in the operation S1000 and the second thermal image generated in the operation S1050. Since the operation S1070 may correspond to the operation S450 of FIG. 4, detailed descriptions thereof will be omitted.

In operation S1080, the controller 230 of the thermal image generating apparatus 200 may display the third thermal image and the image regarding the target object 202, such that the third thermal image and the image overlap each other. In detail, since the image generated by the thermal image generating apparatus 200 in the operation S1060 and the third thermal image generated by the thermal image generating apparatus 200 in the operation S1070 correspond to the same target object 202, the image and the third thermal image may have a same shape. Therefore, if the third thermal image and the image overlap each other, an actual image and a temperature of a particular portion of the target object 202 may be determined simultaneously.

Figure 11:
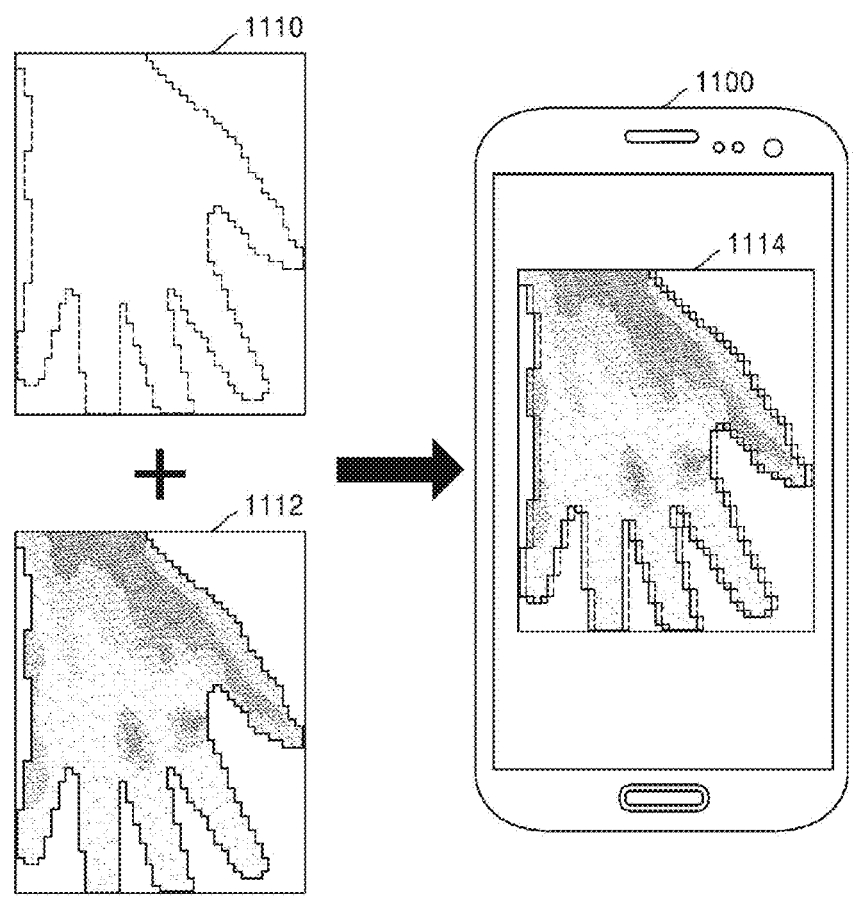
FIG. 11 is a diagram illustrating a process whereby a thermal image generating apparatus overlaps and displays an image and a third thermal image according to an embodiment of the present disclosure.

FIG. 11 is a diagram illustrating a process that a thermal image generating apparatus overlaps and displays an image and a third thermal image according to an embodiment of the present disclosure. The thermal image generating apparatus of FIG. 11 may correspond to the thermal image generating apparatus 200 of FIG. 2.

Referring to FIG. 11, a thermal image generating apparatus 1100 may generate an image 1110 in the operation S1060. Furthermore, the thermal image generating apparatus 1100 may generate a third thermal image 1112 in the operation S1070. The thermal image generating apparatus 1100 may display an overlap image 1114 by overlapping the image 1110 to the third thermal image 1112. A technique for displaying the overlap image 1114 by overlapping the image 1110 to the third thermal image 1112 may be a technique for displaying the image 1110 and the third thermal image 1112 as layers or a technique for overlapping and displaying the image 1110 and the third thermal image 1112 via a separate image processing, but is not limited thereto.

Figure 12:
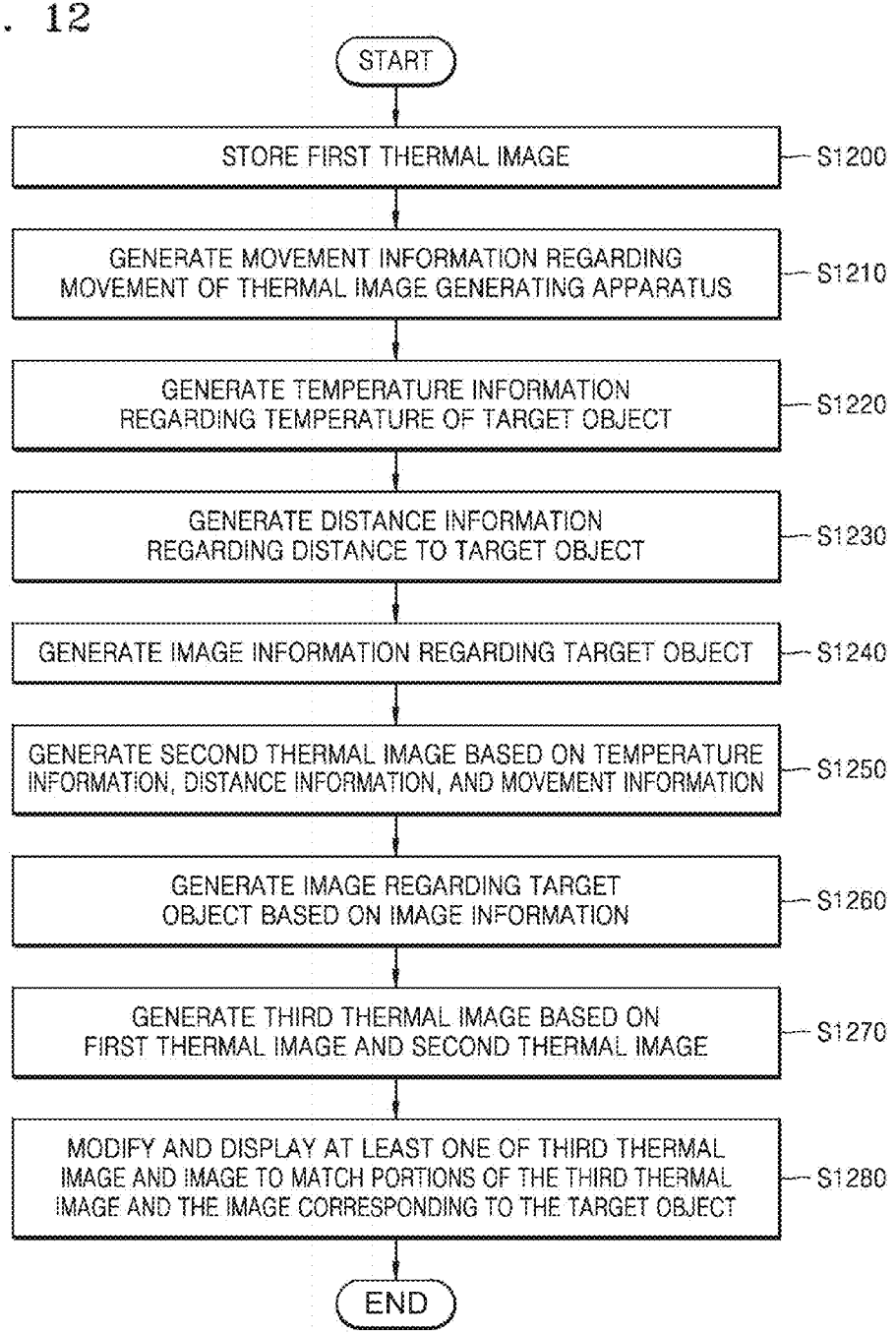
FIG. 12 is a flowchart illustrating a method of generating a thermal image in which the thermal image generating apparatus corrects at least one of a third thermal image and an image so as to correct errors therebetween according to an embodiment of the present disclosure.

FIG. 12 is a flowchart illustrating a method of generating a thermal image according to an embodiment of the present disclosure, in which a thermal image generating apparatus corrects at least one of a third thermal image and an image to correct errors therebetween.

Referring to FIG. 12, in operation S1200, the thermal image generating apparatus 300 may store a first thermal image in the memory 370. Since the operation S1200 may correspond to the operation S400 of FIG. 4, detailed descriptions thereof will be omitted.

In operation S1210, the thermal image generating apparatus 300 may generate movement information regarding a movement of the thermal image generating apparatus 300 by using the third sensor 320. Since the operation S1210 may correspond to the operation S410 of FIG. 4, detailed descriptions thereof will be omitted.

In operation S1220, the thermal image generating apparatus 300 may generate temperature information regarding temperature of the target object 202. Since the operation S1220 may correspond to the operation S420 of FIG. 4, detailed descriptions thereof will be omitted.

In operation S1230, the thermal image generating apparatus 300 may generate distance information regarding a distance between the target object 202 and the thermal image generating apparatus 300. Since the operation S1230 may correspond to the operation S430 of FIG. 4, detailed descriptions thereof will be omitted.

In operation S1240, the thermal image generating apparatus 300 may generate image information by capturing an image of the target object 202. In detail, the thermal image generating apparatus 300 may further include an image capturer 360 capable of receiving visible rays. When the image capturer 360 of the thermal image generating apparatus 300 according to an embodiment of the present disclosure receives visible rays reflected by the target object 202 and transmits data to the controller 330 of the thermal image generating apparatus 300, the controller 330 of the thermal image generating apparatus 300 may generate an image, which is similar to a naked-eye view of the target object 202. The thermal image generating apparatus 300 may also generate image information regarding the target object 202 by detecting infrared rays and receiving visible rays by using an infrared ray sensor (not illustrated) including the first sensor 310 and the second sensor 315 as illustrated in FIG. 10. However, in this case, image quality may be relatively deteriorated. Therefore, the image capturer 360 may be arranged as a component independent from an infrared ray sensor (not illustrated) to capture a high quality image. However, the first sensor 310 and the image capturer 360 may operate at different locations in the thermal image generating apparatus 300. Therefore, in this case, an optical error may occur between a thermal image based on infrared rays detected by the first sensor 310 and an image based on visible rays received by the image capturer 360.

In operation S1250, the thermal image generating apparatus 300 may generate a second thermal image based on temperature information, distance information, and movement information. Since the operation S1250 may correspond to the operation S440 of FIG. 4, detailed descriptions thereof will be omitted.

In operation S1260, the thermal image generating apparatus 300 may generate an image of the target object 202 based on the image information generated by using the image capturer 360 of the thermal image generating apparatus 300 in the operation S1240. Since the operation S1260 may correspond to the operation S1060 of FIG. 10, detailed descriptions thereof will be omitted.

In operation S1270, the thermal image generating apparatus 300 may generate a third thermal image based on the first thermal image stored in the operation S1200 and the second thermal image generated in the operation S1250. Since the operation S1270 may correspond to the operation S450 of FIG. 4, detailed descriptions thereof will be omitted.

In operation S1280, the thermal image generating apparatus 300 may modify and display at least one of the image generated in the operation S1260 and the third thermal image generated in the operation S1270 to match portions of the image and the third thermal image corresponding to the target object.

Figure 13:
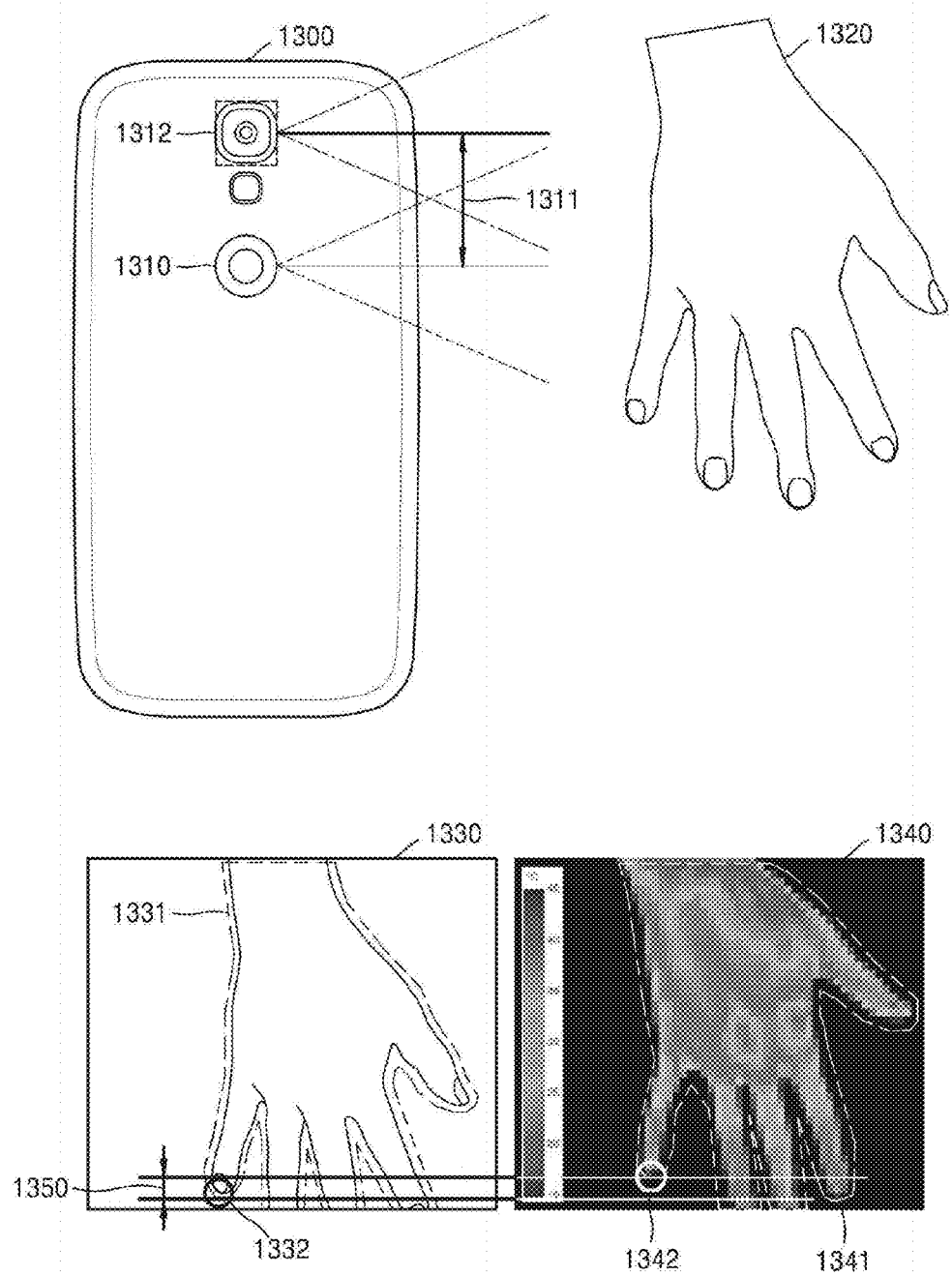
FIG. 13 is a diagram illustrating an error between a thermal image and an image based on a difference between a sensor for measuring temperature information and a sensor for capturing an image to describe a method by which the thermal image generating apparatus corrects locations of an image and a third thermal image according to an embodiment of the present disclosure.

FIG. 13 is a diagram illustrating an error between a thermal image and an image based on a difference between a sensor for measuring temperature information and a sensor for capturing an image to describe a method by which the thermal image generating apparatus corrects locations of an image and a third thermal image according to an embodiment of the present disclosure.

Referring to FIG. 13, a thermal image generating apparatus 1300 may include a first sensor 1310 and an image capturer 1312. The thermal image generating apparatus 1300 of FIG. 13 may correspond to the thermal image generating apparatus 300 of FIG. 3. The first sensor 1310 of FIG. 13 may correspond to the first sensor 310 of FIG. 3. The image capturer 1312 of FIG. 13 may correspond to the image capturer 360 of FIG. 3.

Referring to FIG. 13, according to an embodiment of the present disclosure, the first sensor 1310 and the image capturer 1312 may be arranged at different locations in the thermal image generating apparatus 1300. For example, as illustrated in FIG. 13, the first sensor 1310 and the image capturer 1312 may be a particular distance 1311 apart from each other in a vertical direction. If the thermal image generating apparatus 1300 performs a measurement by using the first sensor 1310 and captures an image by using the image capturer 1312, an error may occur due to the particular distance 1311. Particularly, as in an embodiment of the present disclosure, the shorter the distance between a target object 1320 and the thermal image generating apparatus 1300 is, the greater the error may become. For example, the first sensor 1310 may be located below the image capturer 1312. In this case, a portion 1341 corresponding to the target object 1320 in a third thermal image 1340 may be generated at a horizontally different location that of a portion 1331 corresponding to the target object 1320 in an image 1330 generated by using the image capturer 1312 with respect to the same target object 1320. An error 1350 between the portion 1341 corresponding to the target object 1320 in the third thermal image 1340 and the portion 1331 corresponding to the target object 1320 in the image 1330 may correspond to the particular distance 1311 between the first sensor 1310 and the image capturer 1312. The error 1350 becomes significant when a distance between the target object 1320 and the thermal image generating apparatus 1300 is relatively small. Since measurements are performed at a close distance in various embodiments of the present disclosure, it is necessary to correct the error 1350.

According to an embodiment of the present disclosure, the thermal image generating apparatus 1300 may determine a particular point 1332 at the portion 1341 corresponding to a target object in the third thermal image 1340 and may determine a particular point 1342 at the portion 1331 corresponding to the target object in the image 1330. After the particular points 1332 and 1342 are determined, the controller 330 of the thermal image generating apparatus 1300 may analyze a difference between the particular points 1332 and 1342. Based on a result of the analysis, the controller 330 of the thermal image generating apparatus 1300 may control the display 340 to modify at least one of the image 1330 and the third thermal image 1340, such that the portion 1341 corresponding to the target object in the third thermal image 1340 and the portion 1331 corresponding to the target object in the image 1330 overlap each other more precisely. The controller 330 of the thermal image generating apparatus 1300 may determine the particular points 1332 and 1342 by detecting portions corresponding to the target object 1320 in the image 1330 and the third thermal image 1340 regarding the target object 1320 by using a segmentation technique. In detail, a technique for finding coordinates corresponding to an average of a specific region may be used. Furthermore, an algorithm for finding vertexes may be used at the portions 1331 and 1341 corresponding to the target object in the third thermal image 1340 and the image 1330, and a vertex in the image 1330 and a vertex in the third thermal image 1340 corresponding to each other may be determined as the particular points 1332 and 1342, respectively. However, methods for finding the particular points 1332 and 1342 are not limited thereto. Any of various methods for finding points for comparing an error between the portions 1331 and 1341 corresponding to the target object in the image 1330 and the third thermal image 1340 may be utilized, where each of the image 1330 and the third thermal image 1340 may include at least one particular point.

Figure 14:
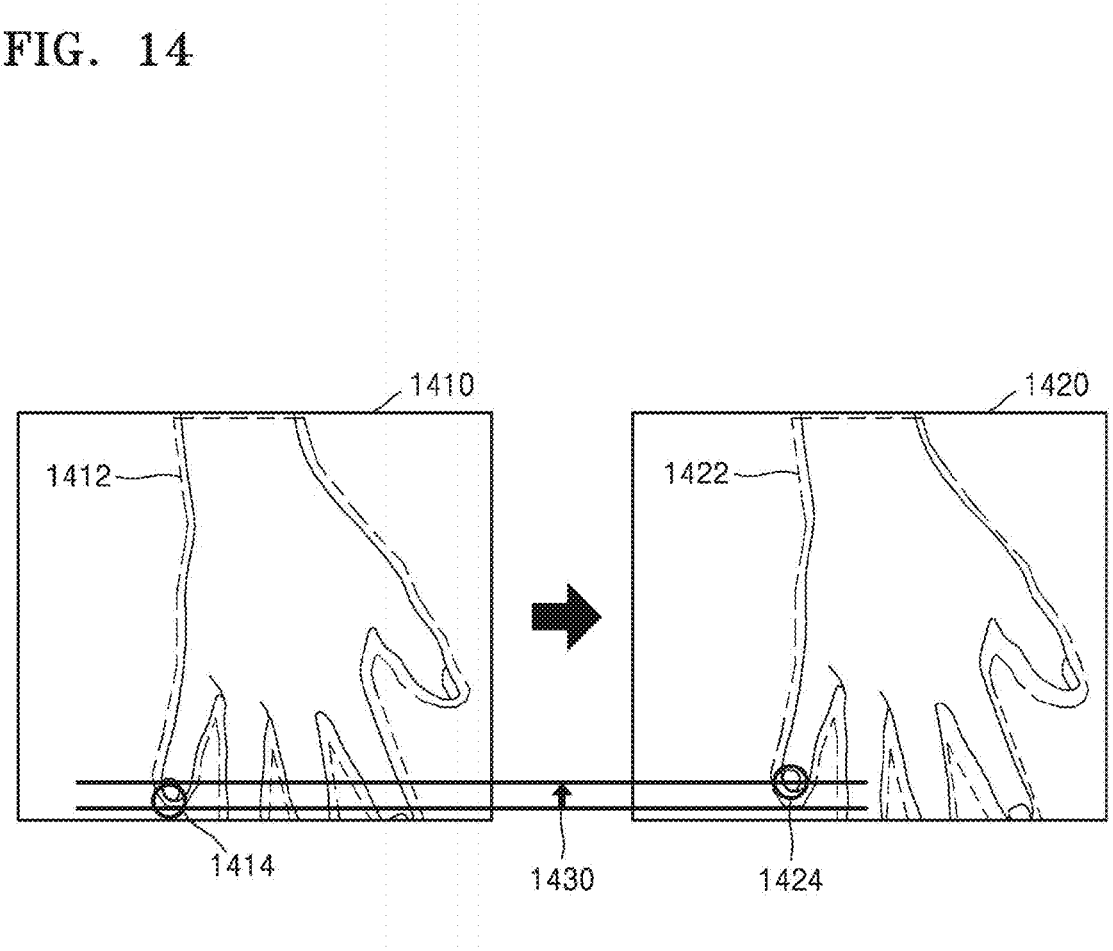
FIG. 14 is a diagram illustrating a process of correcting an error between a third thermal image and an image according to an embodiment of the present disclosure.

FIG. 14 is a diagram illustrating a process for correcting an error between a third thermal image and an image according to an embodiment of the present disclosure.

Referring to FIG. 14, based on the error 1350 between the particular points 1332 and 1342 found in FIG. 13, the error 1350 may be corrected by modifying at least one of the image 1330 and the third thermal image 1340. The controller 330 of the thermal image generating apparatus 1300 may correct the error 1350 by not only modifying the image 1330, but also modifying the third thermal image 1340 or both the image 1330 and the third thermal image 1340 by applying the technique described below as-is or applying a partial modification thereof. For convenience of explanation, a process by which the controller 330 of the thermal image generating apparatus 1300 modifies the image 1330 will be described.

Referring to FIGS. 13 and 14, to correct the error 1350 between the portion 1331 corresponding to the target object in the image 1330 and the portion 1341 corresponding to the target object in the third thermal image 1340, the controller 330 of the thermal image generating apparatus 1300 may modify an image 1410 in correspondence with the error 1350. According to an embodiment of the present disclosure, a target object portion 1412 of the image 1410 may be moved from the first sensor 1310 toward the image capturer 1312 by as much as the error 1350. According to an embodiment of the present disclosure, since the first sensor 1310 is located vertically above the image capturer 1312, the controller 330 may move the target object portion 1412 of the image 1410 vertically upward by as much as the error 1350. In other words, a particular point 1414 of the image 1410 in is moved vertically upward 1430 to become consistent with a particular point 1424 in a target object portion 1422 of a third thermal image 1420.

Figure 15:
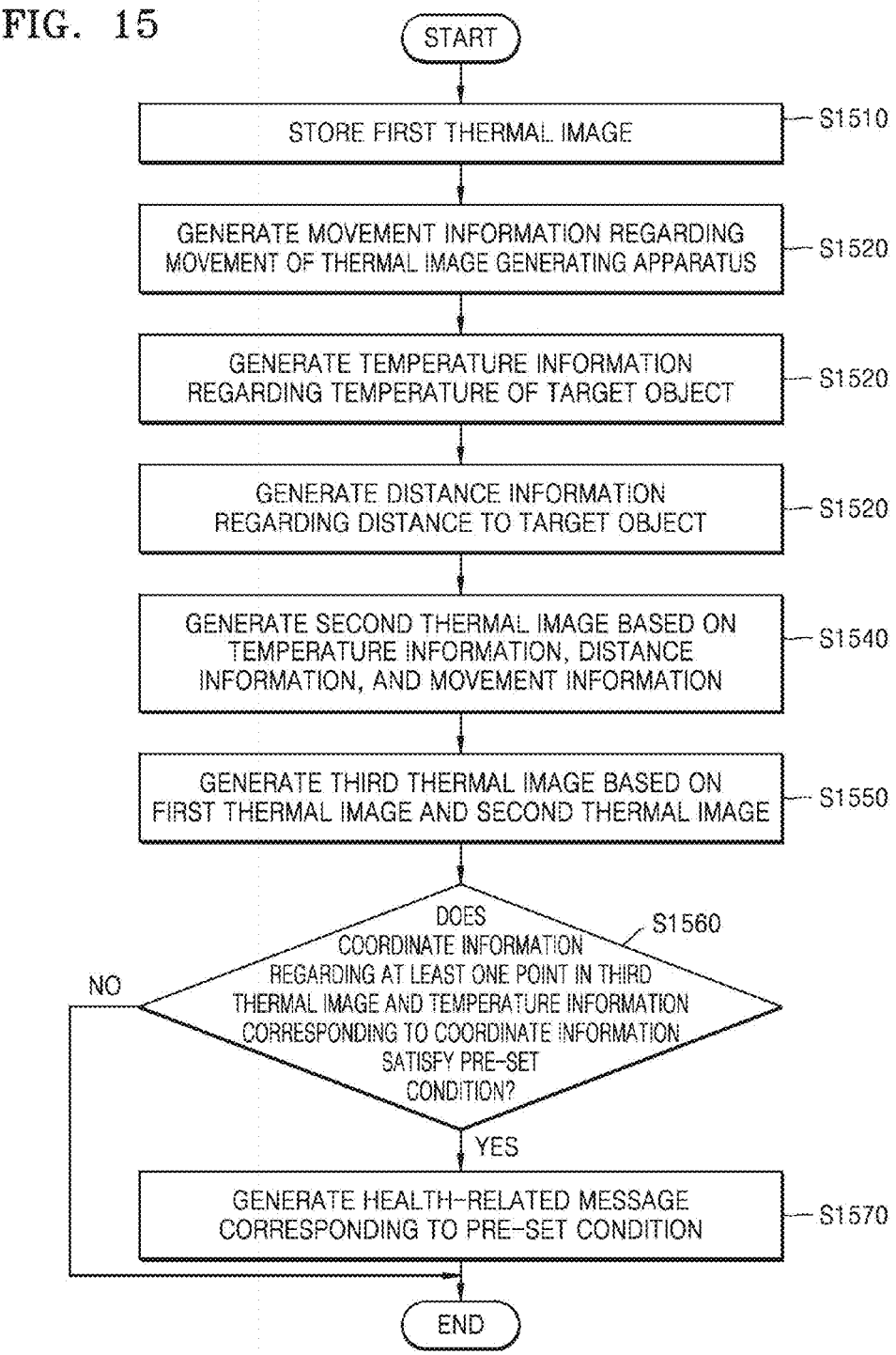
FIG. 15 is a flowchart illustrating a method of generating a thermal image, in which it is determined whether a thermal image generated by the thermal image generating apparatus satisfies a pre-set condition and, if the pre-set condition is satisfied, a health-related message is generated according to an embodiment of the present disclosure.

FIG. 15 is a flowchart illustrating a method of generating a thermal image according to an embodiment of the present disclosure, in which it is determined whether the thermal image generated by a thermal image generating apparatus satisfies a pre-set condition and, if the pre-set condition is satisfied, a health-related message is generated.

Referring to FIG. 15, in detail, if it is determined that a thermal image regarding the target object 202 indicates a particular sign, the controller 230 of the thermal image generating apparatus 200 may generate a health-related message related to the generated third thermal image and the particular sign determined based on the third thermal image.

Figure 16:
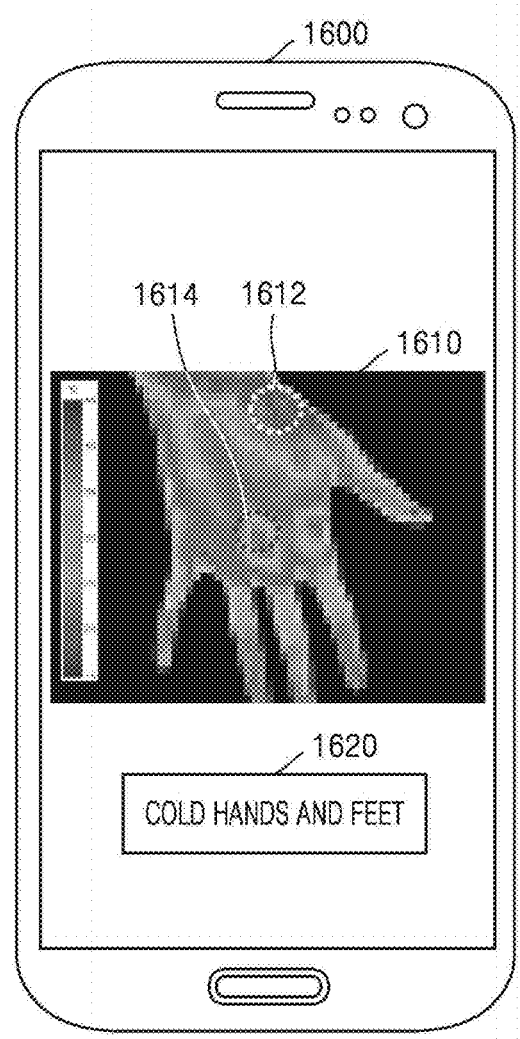
FIG. 16 is a diagram illustrating a thermal image satisfying a pre-set condition and a generated health-related message according to an embodiment of the present disclosure.

FIG. 16 is a diagram illustrating that a thermal image satisfies a pre-set condition and a health-related message is generated according to an embodiment of the present disclosure. A thermal image generating apparatus of FIG. 16 may correspond to the thermal image generating apparatus 300 of FIG. 3. Hereinafter, descriptions will be given with reference to FIG. 16.

Referring to FIGS. 15 and 16, in operation S1500, the thermal image generating apparatus 1600 may store a first thermal image in the memory 240. Since the operation S1500 may correspond to the operation S400 of FIG. 4, detailed descriptions thereof will be omitted.

In operation S1510, a thermal image generating apparatus 1600 may generate movement information regarding a movement of the thermal image generating apparatus 1600 by using the third sensor 220. The movement information may be used to determine a location to apply corresponding temperature information during generation of a thermal image based on a plurality of pieces of thermal image information generated later.

In operation S1520, the thermal image generating apparatus 1600 may generate temperature information regarding temperature of the target object 202 by using the first sensor 210. Since the operation S1520 may correspond to the operation S420 of FIG. 4, detailed descriptions thereof will be omitted.

In operation S1530, the thermal image generating apparatus 1600 may generate distance information regarding a distance between the target object 202 and the first sensor 210 by using the second sensor 215. Since the operation S1530 may correspond to the operation S430 of FIG. 4, detailed descriptions thereof will be omitted.

In operation S1540, the controller 230 of the thermal image generating apparatus 1600 may generate a second thermal image based on the temperature information, the distance information, and the movement information. Since the operation S1540 may correspond to the operation S440 of FIG. 4, detailed descriptions thereof will be omitted.

In operation S1550, the controller 230 of the thermal image generating apparatus 1600 may generate a third thermal image based on the first thermal image stored in the operation S1500 and the second thermal image generated in the operation S1540. Since the operation S1550 may correspond to the operation S450 of FIG. 4, detailed descriptions thereof will be omitted.

In operation S1560, the controller 230 of the thermal image generating apparatus 1600 may determine coordinate information regarding at least one point in a thermal image and temperature information corresponding to the coordinate information satisfy a pre-set condition.

Referring to FIG. 16, the controller 230 of the thermal image generating apparatus 1600 may measure temperature of a person's hand as the target object 202. The controller 230 of the thermal image generating apparatus 1600 may detect coordinate information regarding a first location 1612 and a second location 1614 of the target object 202, analyze temperature information corresponding to the first location 1612 and the second location 1614, and determine whether a pre-set condition is satisfied. For example, the pre-set condition may be a case in which a difference between a temperature of the first location 1612 corresponding to the point with the highest temperature in a third thermal image 1610 corresponding to a hand (the target object 202) and a temperature of the second location 1614 corresponding to the point with the lowest temperature in the third thermal image 1610 is greater than a critical temperature and a case in which a distance between coordinates of the first location 1612 and coordinates of the second location 1614 is greater than a critical distance.

In operation S1570, if it is determined in the operation S1560 that the pre-set condition is satisfied, the controller 230 of the thermal image generating apparatus 1600 may generate a health-related message 1620 related to the third thermal image 1610. According to an embodiment of the present disclosure, if the controller 230 of the thermal image generating apparatus 1600 determines that the pre-set condition is satisfied as a difference between a temperature of the first location 1612 corresponding to the point with the highest temperature in the third thermal image 1610 corresponding to the hand (the target object 202) and a temperature of the second location 1614 corresponding to the point with the lowest temperature in the third thermal image 1610 is greater than a critical temperature and a distance between coordinates of the first location 1612 and coordinates of the second location 1614 is greater than a critical distance, a health-related message 1620 related to cold hands and feet may be generated. According to an embodiment of the present disclosure, the controller 230 of the thermal image generating apparatus 1600 may control the display 340 to display the third thermal image 1610 together with the health-related message 1620 corresponding to the third thermal image 1610. According to an embodiment of the present disclosure, if the controller 230 of the thermal image generating apparatus 1600 determines that the third thermal image 1610 satisfies a pre-set condition, the controller 230 of the thermal image generating apparatus 1600 may control the communicator 350 to transmit health-related information 1620 to a hospital-related server (not illustrated). According to an embodiment of the present disclosure, the thermal image generating apparatus 1600 may generate the third thermal image 1610 related to a patient and transmits a health-related message regarding the corresponding patient together with the third thermal image 1610 to a hospital server, and thus a doctor may quickly and precisely perform a remote diagnosis.

Figure 17:
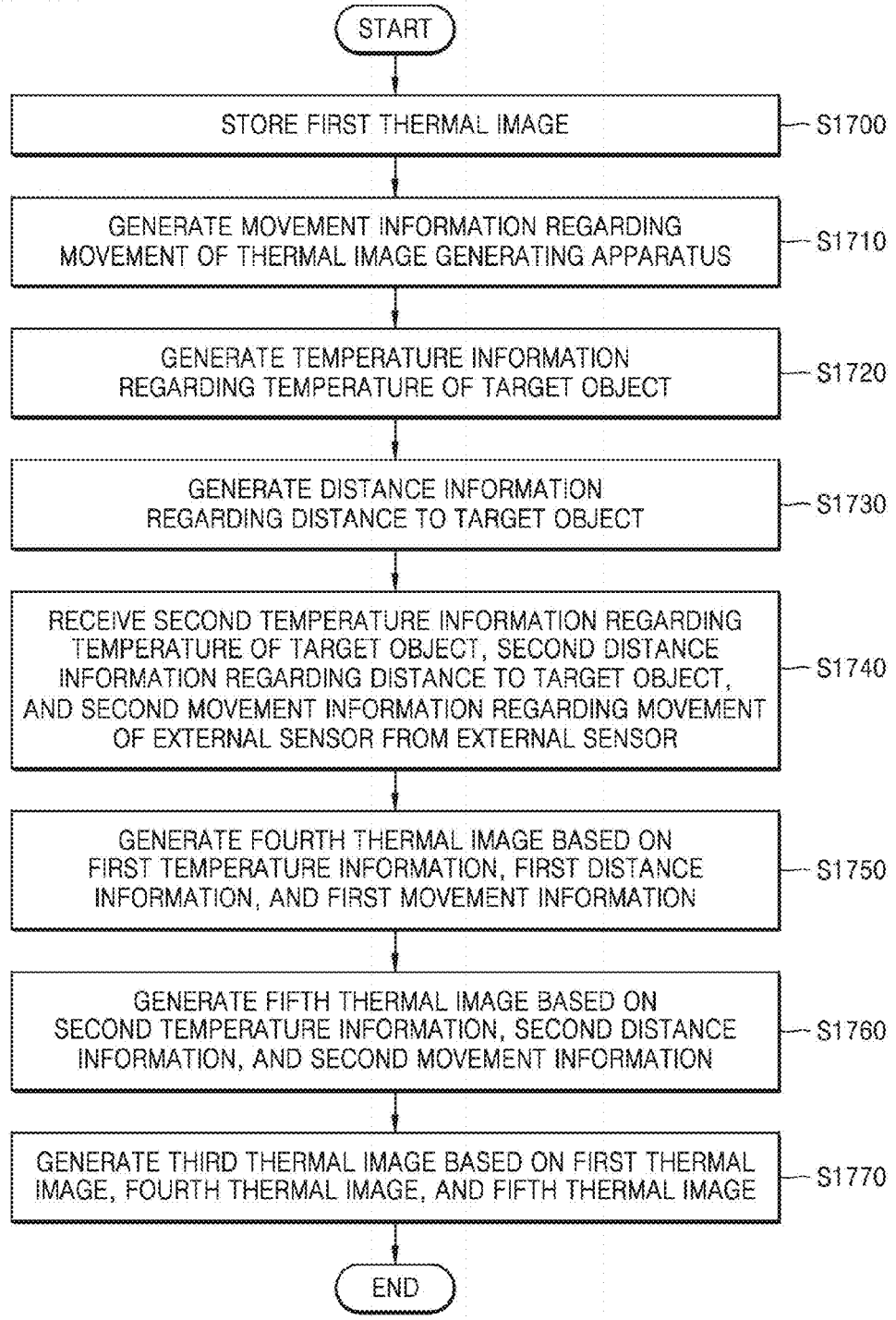
FIG. 17 is a flowchart illustrating a method of generating a thermal image, in which a thermal image is generated by using a thermal image generating apparatus and an external sensor according to an embodiment of the present disclosure.

FIG. 17 is a flowchart illustrating a method of generating a thermal image according to an embodiment of the present disclosure, in which a thermal image is generated by using a thermal image generating apparatus and an external sensor.

Referring to FIG. 17, in detail, the thermal image generating apparatus 300 may generate a third thermal image based on first temperature information, first distance information, and first movement information respectively received from the first sensor 310, the second sensor 315, and the third sensor 320. However, the thermal image generating apparatus 300 may also generate a third thermal image by using second temperature information, second distance information, and second movement information received from an external sensor outside the thermal image generating apparatus 300. Here, the first temperature information, the first distance information, and the first movement information may correspond to the temperature information, the distance information, and the movement information described above with reference to FIG. 2, respectively.

Figure 18:
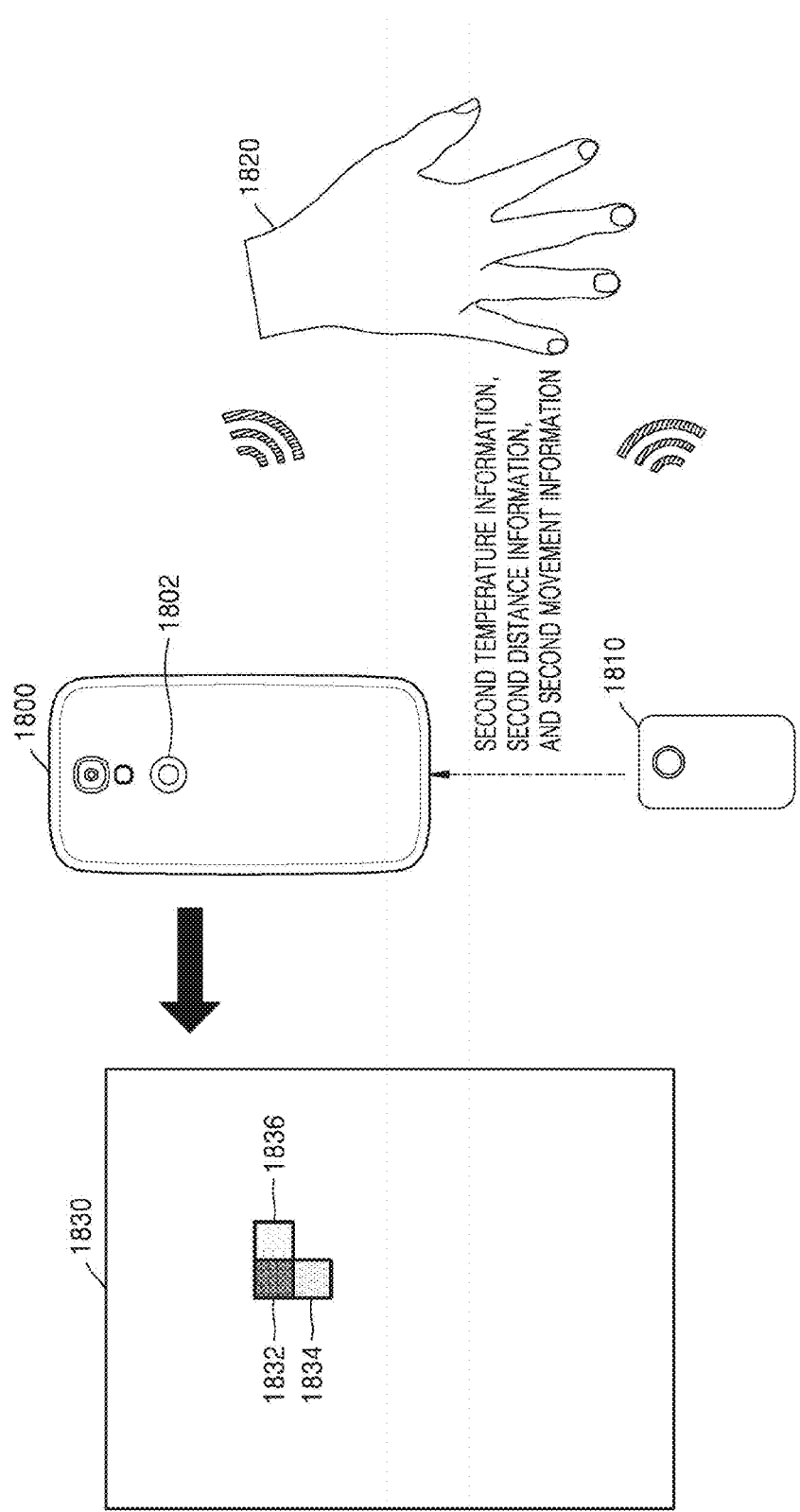
FIG. 18 is a diagram illustrating a process in which a thermal image generating apparatus generates a fourth thermal image based on first temperature information, first distance information, and first movement information and generates a fifth thermal image based on second temperature information, second distance information, and second movement information received from an external sensor according to an embodiment of the present disclosure.

FIG. 18 is a diagram illustrating a process in which a thermal image generating apparatus 1800 according to an embodiment of the present disclosure generates a fourth thermal image based on first temperature information, first distance information, and first movement information and generates a fifth thermal image based on second temperature information, second distance information, and second movement information received from an external sensor. The thermal image generating apparatus 1800 of FIG. 18 may correspond to the thermal image generating apparatus 300 of FIG. 3. Hereinafter, descriptions will be given with reference to FIG. 18.

Referring to FIGS. 17 and 18, in operation S1700, the thermal image generating apparatus 1800 may store a first thermal image in the memory 240. Since the operation S1700 may correspond to the operation S400 of FIG. 4, detailed descriptions thereof will be omitted.

In operation S1710, the thermal image generating apparatus 1800 may generate first movement information regarding a movement of the thermal image generating apparatus 1800 by using the third sensor 320. Since the operation S1710 may correspond to the operation S410 of FIG. 4, detailed descriptions thereof will be omitted.

In operation S1720, the thermal image generating apparatus 1800 may generate first temperature information regarding temperature of a target object 1820 by using a first sensor 1802. Since the operation S1720 may correspond to the operation S420 of FIG. 4, detailed descriptions thereof will be omitted.

In operation S1730, the thermal image generating apparatus 1800 may generate first distance information regarding a distance between the target object 1820 and the third sensor 320. Since the operation S1730 may correspond to the operation S430 of FIG. 4, detailed descriptions thereof will be omitted.

In operation S1740, the thermal image generating apparatus 1800 may receive second temperature information, second distance information, and second movement information from an external sensor 1810. The second temperature information, the second distance information, and the second movement information generated by the external sensor 1810 may be in the same formats as the first temperature information, the first distance information, and the first movement information generated by the thermal image generating apparatus 1800. According to an embodiment of the present disclosure, the second temperature information, the second distance information, and the second movement information may be generated as the external sensor 1810 performs operations corresponding the operations S410, S420, and S430 of FIG. 4, respectively.

In operation S1750, the controller 330 of the thermal image generating apparatus 1800 may generate a fourth thermal image based on the first temperature information, the first distance information, and the first movement information.

Referring to FIG. 18, according to an embodiment of the present disclosure, the memory 370 of the thermal image generating apparatus 1800 may store a first thermal image 1832. The controller 330 of the thermal image generating apparatus 1800 may generate a fourth thermal image 1834 based on first temperature information, first distance information, and first movement information generated with respect to the target object 1820. Since the operation S1750 may correspond to the operation S440 of FIG. 4, detailed descriptions thereof will be omitted.

In operation S1760, the controller 330 of the thermal image generating apparatus 1800 may generate a fifth thermal image 1836 based on second temperature information, second distance information, and second movement information. Generation of a thermal image based on temperature information, distance information, and movement information may correspond to the operation S440 of FIG. 4. According to an embodiment of the present disclosure, the controller 330 of the thermal image generating apparatus 1800 may determine a display location and a display area regarding the fifth thermal image 1836 based on the second temperature information, the second distance information, and the second movement information received from the external sensor 1810 in relation to the first thermal image 1832. Since the operation S1760 may correspond to the operations S550 and S560 of FIG. 5, detailed descriptions thereof will be omitted.

In operation S1770, the controller 330 of the thermal image generating apparatus 1800 may generate a third thermal image 1830 based on the first thermal image stored in the operation S1700, the fourth thermal image generated in the operation S1750, and the fifth thermal image 1836 generated in the operation S1760. According to an embodiment of the present disclosure, a process that the controller 330 of the thermal image generating apparatus 1800 generates the third thermal image based on the fourth thermal image generated in the operation S1750 or the fifth thermal image 1836 generated in the operation S1760 may correspond to the operation S450 of FIG. 4. According to an embodiment of the present disclosure, the third thermal image generated by the controller 330 of the thermal image generating apparatus 1800, based on the fourth thermal image and the fifth thermal image 1836, may include more temperature information than thermal images corresponding to cases where temperatures are measured by using the thermal image generating apparatus 1800 only or temperatures are measured by using the external sensor 1810 only.

Figure 19:
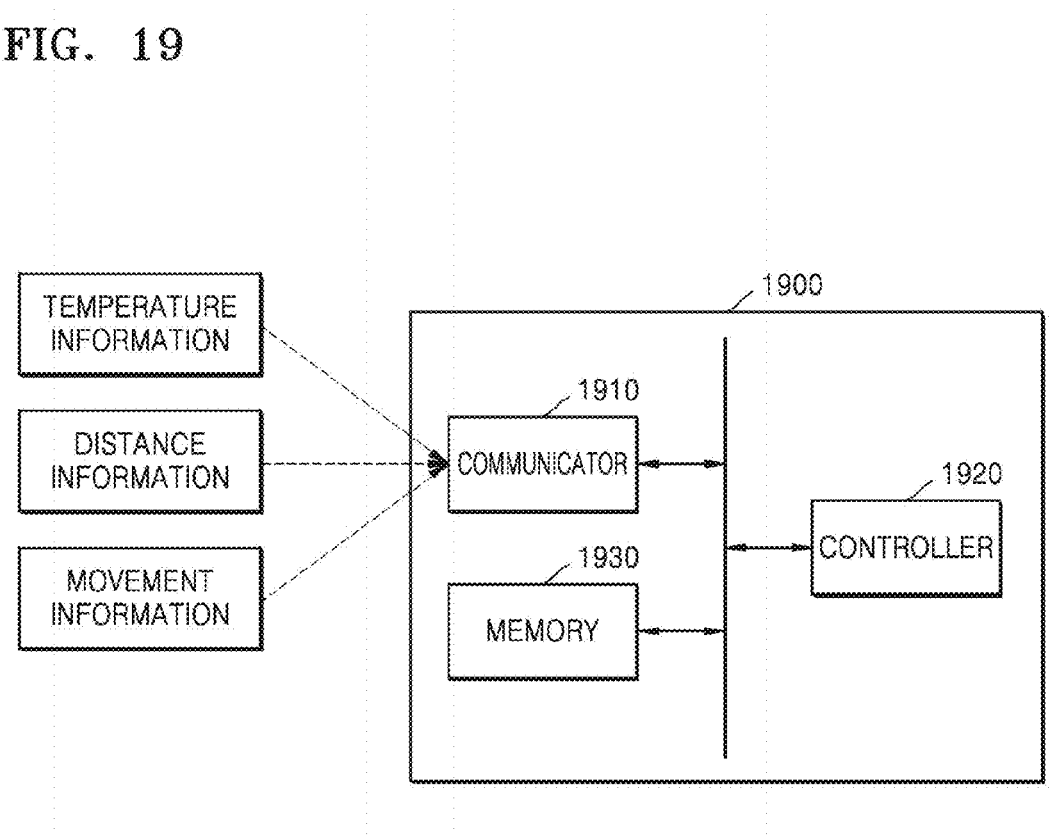
FIG. 19 is a block diagram of a thermal image generating apparatus according to an embodiment of the present disclosure.

FIG. 19 is a block diagram of a thermal image generating apparatus according to an embodiment of the present disclosure.

Referring to FIG. 19, in detail, according to an embodiment of the present disclosure, configuration of a thermal image generating apparatus 1900 of FIG. 19 is different from that of the thermal image generating apparatus 200 of FIG. 2. The thermal image generating apparatus 1900 may store a first thermal image in a memory 1930. The memory 1930 of FIG. 19 may correspond to the memory 240 of FIG. 2. A controller 1920 of the thermal image generating apparatus 1900 may control a communicator 1910 to receive temperature information 1912, distance information 1914, and movement information 1916 from other devices. The controller 1920 of the thermal image generating apparatus 1900 may generate a first thermal image based on received temperature information 1912, distance information 1914, and movement information 1916 and generate a thermal image based on a first thermal image and a second thermal image.

Figure 20:
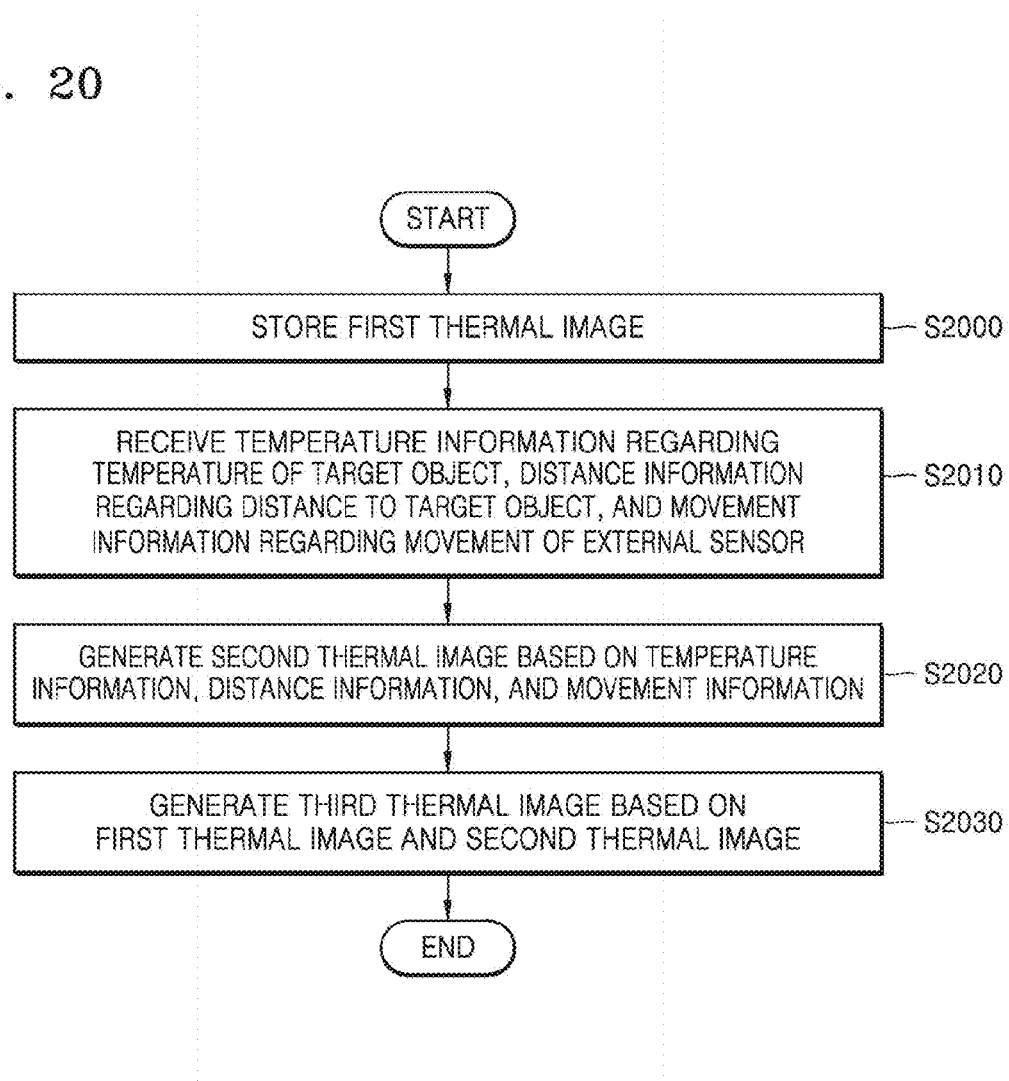
FIG. 20 is a flowchart illustrating a method of generating a thermal image according to an embodiment of the present disclosure.

FIG. 20 is a flowchart illustrating a method of generating a thermal image according to an embodiment of the present disclosure.

Referring to FIG. 20, in other words, it is a flowchart illustrating a method by which a thermal image generating apparatus generates a thermal image.

FIG. 21 is a diagram illustrating a process in which a thermal image generating apparatus receives temperature information, distance information, and movement information from an external sensor and generates a thermal image according to an embodiment of the present disclosure. Descriptions will be given with reference to FIG. 21. A thermal image generating apparatus 2100 of FIG. 21 may correspond to the thermal image generating apparatus 1900 of FIG. 19.

Referring to FIGS. 20 and 21, in operation S2000, the controller 1920 of the thermal image generating apparatus 2100 may control the memory 1930 to store a first thermal image. Since the operation S2000 may correspond to the operation S400 of FIG. 4, detailed descriptions thereof will be omitted.

In operation S2010, the controller 1920 of the thermal image generating apparatus 2100 may control the communicator 1910 to receive temperature information regarding temperature of a target object, distance information regarding a distance to the target object, and movement information regarding a movement of an external sensor. Unlike the thermal image generating apparatus 200 of FIG. 2, the thermal image generating apparatus 2100 does not perform operations corresponding to the operations S410, S420, and S430 of FIG. 4. According to an embodiment of the present disclosure, the controller 1920 of the thermal image generating apparatus 2100 may control the communicator 1910 to receive temperature information 1912 and distance information 1914 corresponding to results of temperature and distance measurements performed with respect to a target object 2120 by an external sensor 2110 outside the thermal image generating apparatus 2100. Furthermore, the controller 1920 of the thermal image generating apparatus 2100 may control the communicator 1910 to receive movement information 1916, which is information regarding a movement of the external sensor 2110 during the temperature and distance measurements with respect to the target object 2120.

In operation S2020, the controller 1920 of the thermal image generating apparatus 2100 may generate a second thermal image based on temperature information, distance information, and movement information received in the operation S2010. According to an embodiment of the present disclosure, the thermal image generating apparatus 2100 may receive temperature information 1912 and distance information 1914 regarding the target object 2120 and movement information 1916 regarding a movement of the external sensor 2110 during measurements with respect to the target object 2120 from the external sensor 2110. Since the operation S2020 may correspond to the operation S440 of FIG. 4, detailed descriptions thereof will be omitted.

In operation S2030, the controller 1920 of the thermal image generating apparatus 2100 may generate a third thermal image 2130 based on the first thermal image stored in the operation S2000 and the second thermal image generated in the operation S2020. Since the operation S2030 may correspond to the operation S450 of FIG. 4, detailed descriptions thereof will be omitted.

The present disclosure may be implemented as computer-readable codes stored on a non-transitory computer-readable recording medium. The non-transitory computer-readable medium may be any medium that may store or transmit computer-readable data.

The computer-readable codes are written to perform operations for embodying an object arranging method according to the present disclosure when read out from the non-transitory computer-readable recording medium and executed by a processor. The computer-readable codes may be written in any of various programming languages. Furthermore, functional programs, codes, and code segments for accomplishing various embodiments of the present disclosure may be easily construed by programmers of ordinary skill in the art to which the present disclosure pertains Examples of the non-transitory computer readable recording medium include ROM, RAM, compact disc ROMs (CD-ROMs), magnetic tapes, floppy disks, optical data storage devices, and the like. The non-transitory computer readable recording medium may also be distributed over network coupled computer systems so that the computer readable code is stored and executed in a distributed fashion.

It should be understood that the various embodiments of the present disclosure described herein should be considered in a descriptive sense only and not for purposes of limitation. Descriptions of features or aspects within each embodiment should typically be considered as available for other similar features or aspects in other embodiments of the present disclosure.

While the present disclosure has been illustrated and described with reference to various embodiments thereof, it will be understood by those skilled in the art that various changes in form and details may be made therein without departing from the spirit and scope of the present disclosure as defined by the appended claims and their equivalents.

What is claimed is:

1. An apparatus for generating a thermal image regarding a target object, the apparatus comprising:
a memory configured to store a first thermal image;
a first sensor configured to measure a temperature of the target object;
a second sensor configured to measure a distance to the target object;
a third sensor configured to detect a movement of the thermal image generating apparatus;
a controller configured to:
generate a second thermal image based on temperature information received from the first sensor, distance information received from the second sensor, and movement information received from the third sensor, and
generate a third thermal image based on the first thermal image and the second thermal image; and
a display configured to display the third thermal image,
wherein the distance information includes measured distances between the thermal image generating apparatus and the target object, and
wherein the controller is further configured to:
compare the distance information related to the second thermal image and distance information related to a portion of the first thermal image overlapping with the second thermal image,
when, a measured distance between the thermal image generating apparatus and the target object at which the second thermal image is generated is shorter than a measured distance between the thermal image generating apparatus and the target object at which the first thermal image is generated, generate the third thermal image by replacing the portion of the first thermal image with the second thermal image, and
when the measured distance at which the second thermal image is generated is longer than or equal to the measured distance at which the first thermal image is generated, not replace the portion of the first thermal image with the second thermal image.

2. The apparatus of claim 1, wherein the controller is further configured to:
determine a display location to display the second thermal image in relation to the first thermal image based on the movement information,
determine a display area to display the second thermal image based on the distance information, and
generate the third thermal image based on the display location and the display area.

3. The apparatus of claim 1, wherein the first sensor and the second sensor are included in an infrared ray sensor configured to:
measure the temperature of the target object, and
measure the distance to the target object.

4. The apparatus of claim 1, further comprising:
an image capturer configured to capture images regarding the target object,
wherein the controller is further configured to:
control the image capturer to capture images regarding the target object, and
control the display to overlap and display the images and the third thermal image.

5. The apparatus of claim 4, wherein the controller is further configured to control the display to modify and display at least one of the third thermal image and the images to match portions of the third thermal image and the images corresponding to the target object.

6. The apparatus of claim 1, wherein, if a pre-set condition determined in advance is satisfied by coordinate information regarding a plurality of points in the third thermal image and temperature information corresponding to the coordinate information, the controller is further configured to generate a health-related message corresponding to the third thermal image and the pre-set condition.

7. The apparatus of claim 1, further comprising:
a communicator configured to receive second temperature information regarding a temperature of the target object, second distance information regarding a distance to the target object, and second movement information regarding a movement of an external sensor for measuring the distance from the external sensor,
wherein the controller is further configured to:
generate a fourth thermal image based on first temperature information received from the first sensor, first distance information received from the second sensor, and first movement information received from the third sensor,
generate a fifth thermal image based on the second distance information, the second temperature information, and the second movement information, and
generate the third thermal image based on the first thermal image, the fourth thermal image, and the fifth thermal image.

8. An apparatus for generating a thermal image regarding a target object, the apparatus comprising:
a memory configured to store a first thermal image;
a communicator configured to receive temperature information regarding a temperature of the target object, distance information regarding a distance to the target object, and movement information regarding a movement of an external sensor from the external sensor;
a controller configured to:
generate a second thermal image based on the temperature information, the distance information, and the movement information received from the external sensor, and
generate a third thermal image based on the first thermal image and the second thermal image; and
a display configured to display the third thermal image,
wherein the distance information includes measured distances between the thermal image generating apparatus and the target object, and
wherein the controller is further configured to:
compare the distance information related to the second thermal image and distance information related to a portion of the first thermal image overlapping with the second thermal image,
when, a measured distance between the thermal image generating apparatus and the target object at which the second thermal image is generated is shorter than a measured distance between the thermal image generating apparatus and the target object at which the first thermal image is generated, generate the third thermal image by replacing the portion of the first thermal image with the second thermal image, and
when the measured distance at which the second thermal image is generated is longer than or equal to the measured distance at which the first thermal image is generated, not replace the portion of the first thermal image with the second thermal image.

9. The apparatus of claim 8, wherein the controller is further configured to:
determine a display location to display the second thermal image in relation to the first thermal image based on the movement information, determines a display area to display the second thermal image based on the distance information, and,
generate, if the second thermal image is generated at a location overlapping the first thermal image, the third thermal image based on distance information corresponding to a shorter distance to the target object from between the distance information regarding the first thermal image and the distance information regarding the second thermal image.

10. A method, performed by a thermal image generating apparatus, of generating a thermal image regarding a target object, the method comprising:
storing a first thermal image;
processing temperature information regarding a temperature of the target object;
processing distance information regarding a distance between the thermal image generating apparatus and the target object;
processing movement information regarding a movement of the thermal image generating apparatus;
generating a second thermal image based on the processed temperature information, the processed distance information, and the processed movement information;
generating a third thermal image based on the first thermal image and the second thermal image; and
displaying the third thermal image,
wherein the distance information includes measured distances between the thermal image generating apparatus and the target object, and
wherein the generating the third thermal image comprises:
comparing the distance information related to the second thermal image and distance information related to a portion of the first thermal image overlapping with the second thermal image;
when, a measured distance between the thermal image generating apparatus and the target object at which the second thermal image is generated is shorter than a measured distance between the thermal image generating apparatus and the target object at which the first thermal image is generated, generating the third thermal image by replacing the portion of the first thermal image with the second thermal image, and
when the measured distance at which the second thermal image is generated is longer than or equal to the measured distance at which the first thermal image is generated, generating the third thermal image using the first thermal image.

11. The method of claim 10, wherein the temperature information, the distance information, and the movement information are received from an external sensor.

12. The method of claim 10, wherein the generating of the third thermal image comprises:
determining a display location to display the second thermal image in relation to the first thermal image based on the movement information;
determining a display area to display the second thermal image based on the distance information; and
generating the third thermal image based on the display location and the display area.

13. The method of claim 10, wherein the temperature of the target object and the distance to the target object are measured by using an infrared ray sensor.

14. The method of claim 10, further comprising:
capturing images regarding the target object; and displaying the images and the third thermal image, such that the images overlap the third thermal image.

15. The method of claim 14, wherein the displaying of the images and the third thermal image comprises modifying and displaying at least one of the third thermal image and the images to match portions of the third thermal image and the images corresponding to the target object.

16. The method of claim 10, further comprising:
determining whether a pre-set condition determined in advance is satisfied by coordinate information regarding a plurality of points in the third thermal image and temperature information corresponding to the coordinate information; and,
generating, if the pre-set condition is satisfied, a health-related message corresponding to the third thermal image and the pre-set condition.

17. The method of claim 10, further comprising:
receiving second temperature information regarding a temperature of the target object, second distance information regarding a distance to the target object, and second movement information regarding a movement of an external sensor for measuring the distance from the external sensor;
generating a fourth thermal image based on first temperature information received from the first sensor, first distance information received from the second sensor, and first movement information received from the third sensor, generating a fifth thermal image based on the second distance information, the second temperature information, and the second movement information; and
generating the third thermal image based on the first thermal image, the fourth thermal image, and the fifth thermal image.

18. A non-transitory computer readable recording medium having recorded thereon a computer program for implementing the method of claim 10.

* * * * *